United States Patent
Nagasu et al.

(10) Patent No.: US 10,040,278 B2
(45) Date of Patent: Aug. 7, 2018

(54) CONVEYED OBJECT DETECTION APPARATUS, CONVEYANCE APPARATUS, AND CONVEYED OBJECT DETECTION METHOD

(71) Applicants: Tsuyoshi Nagasu, Kanagawa (JP); Koichi Kudo, Kanagawa (JP)

(72) Inventors: Tsuyoshi Nagasu, Kanagawa (JP); Koichi Kudo, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 15/456,677

(22) Filed: Mar. 13, 2017

(65) Prior Publication Data
US 2017/0266954 A1    Sep. 21, 2017

(30) Foreign Application Priority Data

Mar. 15, 2016 (JP) .................. 2016-051470
Feb. 24, 2017 (JP) .................. 2017-034105

(51) Int. Cl.
| | |
|---|---|
| *B41J 2/045* | (2006.01) |
| *B41J 11/00* | (2006.01) |
| *B41J 11/42* | (2006.01) |
| *B65H 43/08* | (2006.01) |
| *B65H 20/02* | (2006.01) |

(52) U.S. Cl.
CPC .......... *B41J 2/04505* (2013.01); *B65H 20/02* (2013.01); *B65H 43/08* (2013.01); *B65H 2801/06* (2013.01)

(58) Field of Classification Search
CPC ...... B41J 2/04505; B41J 11/42; B41J 11/005; B41J 11/0095
See application file for complete search history.

(56) References Cited

U.S. PATENT DOCUMENTS

| | | |
|---|---|---|
| 9,028,027 B2 | 5/2015 | Bell et al. |
| 9,440,431 B2 | 9/2016 | Hommi |
| 2005/0190248 A1* | 9/2005 | Konno ............ B41J 2/155 347/102 |

(Continued)

FOREIGN PATENT DOCUMENTS

| | | |
|---|---|---|
| JP | 2014-035197 | 2/2014 |
| JP | 2015-013476 | 1/2015 |

OTHER PUBLICATIONS

U.S. Appl. No. 15/294,904, filed Oct. 17, 2016.
(Continued)

*Primary Examiner* — Jason Uhlenhake
(74) *Attorney, Agent, or Firm* — IPUSA, PLLC

(57) ABSTRACT

A conveyed object detection apparatus includes an optical sensor configured to receive light reflected by a conveyed object; a detection unit configured to use the optical sensor to acquire a detection result indicating a position, a moving speed, or a moved amount of the conveyed object in at least one of a conveyance direction in which the conveyed object is conveyed and a direction perpendicular to the conveyance direction, or a combination of the position, the moving speed, and the moved amount; and a setting unit configured to set an aperture value and an exposure time concerning the optical sensor based on the detection result.

17 Claims, 28 Drawing Sheets

(56) References Cited

U.S. PATENT DOCUMENTS

| | | | |
|---|---|---|---|
| 2009/0002424 A1* | 1/2009 | Kiyama | B41J 3/543 |
| | | | 347/16 |
| 2014/0044460 A1* | 2/2014 | Kudo | G03G 15/5054 |
| | | | 399/301 |
| 2016/0011009 A1 | 1/2016 | Shimizu et al. | |
| 2016/0121602 A1 | 5/2016 | Nagasu et al. | |

OTHER PUBLICATIONS

U.S. Appl. No. 15/373,807, filed Dec. 9, 2016.
U.S. Appl. No. 15/373,825, filed Dec. 9, 2016.
U.S. Appl. No. 15/455,539, filed Mar. 10, 2017.

\* cited by examiner 210K-1

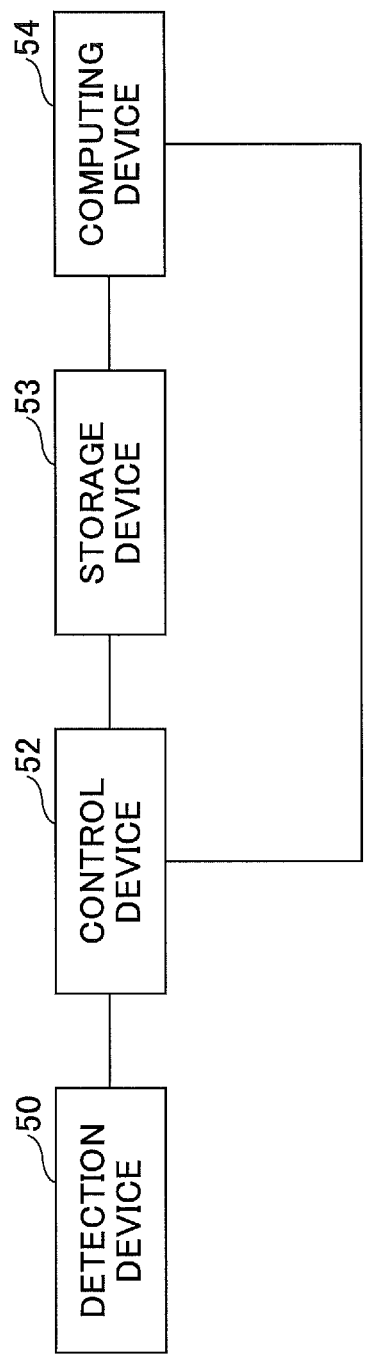

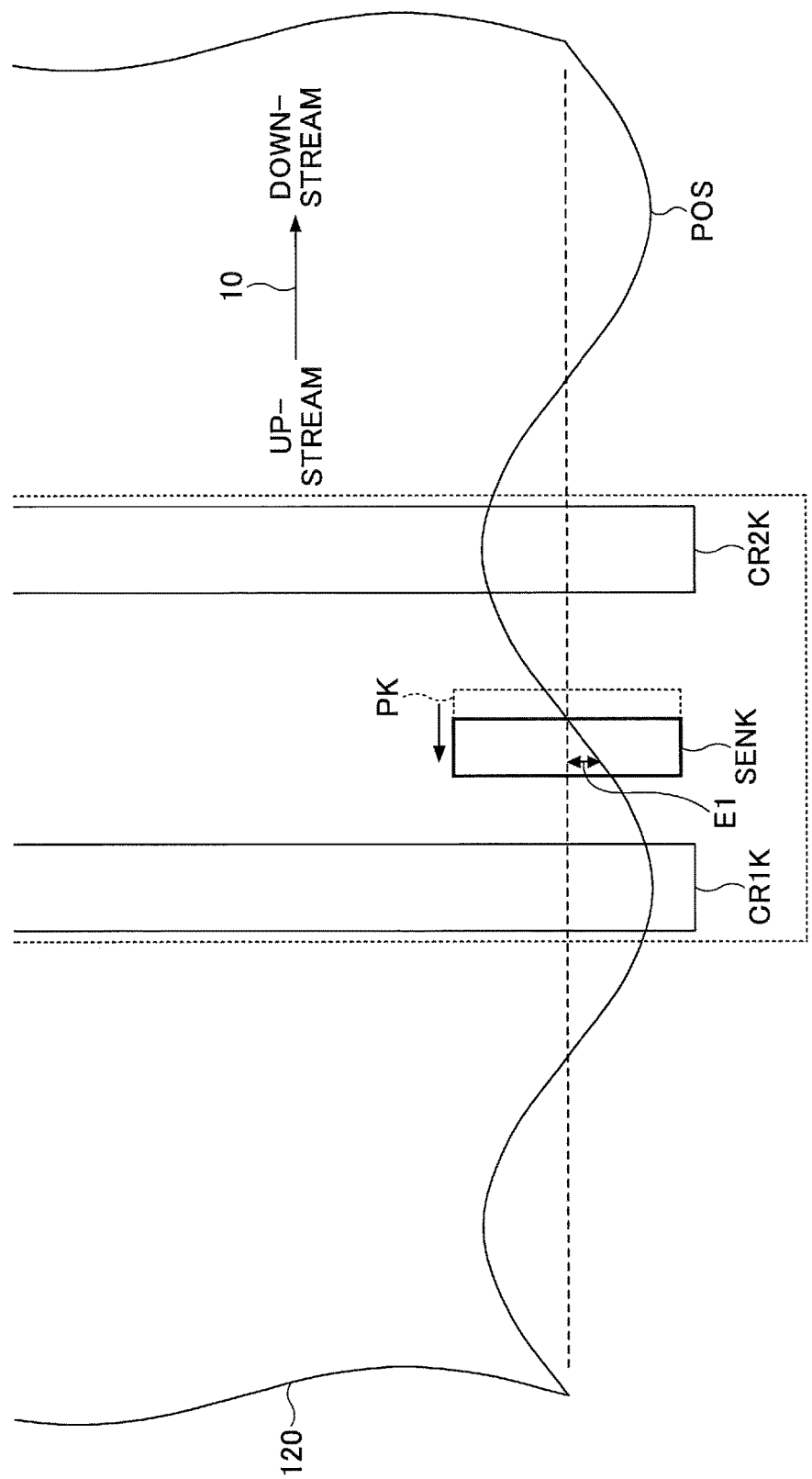

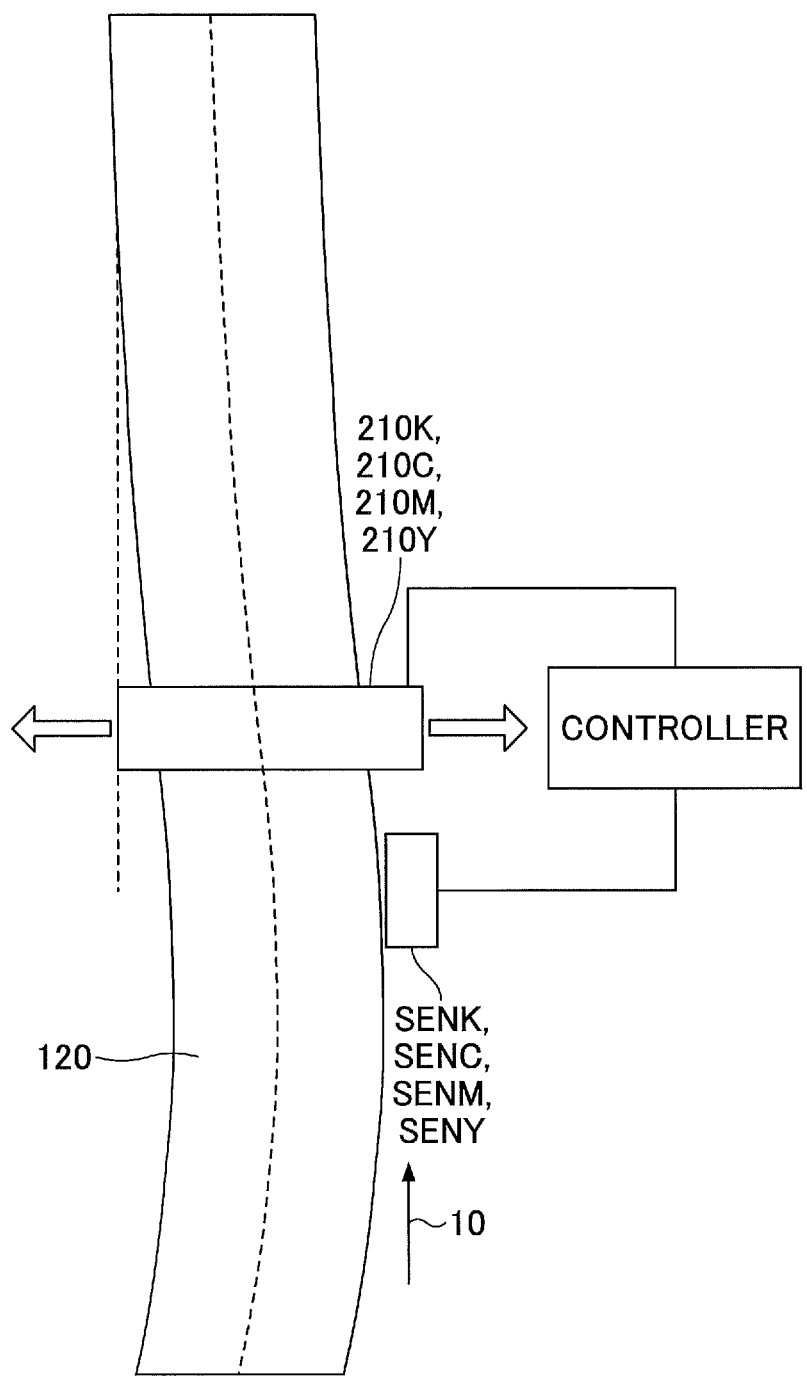

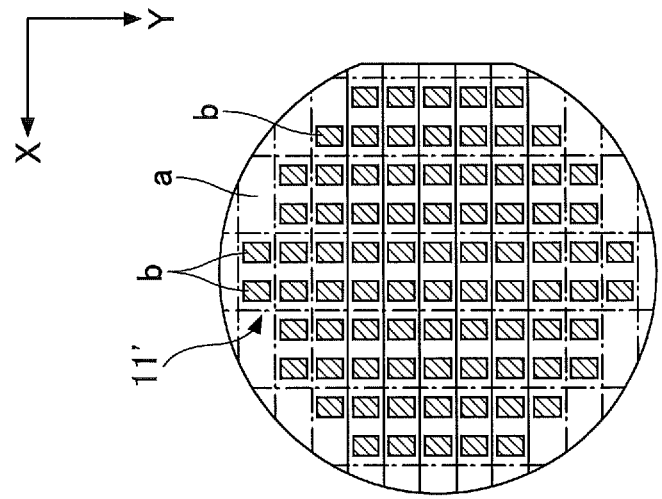
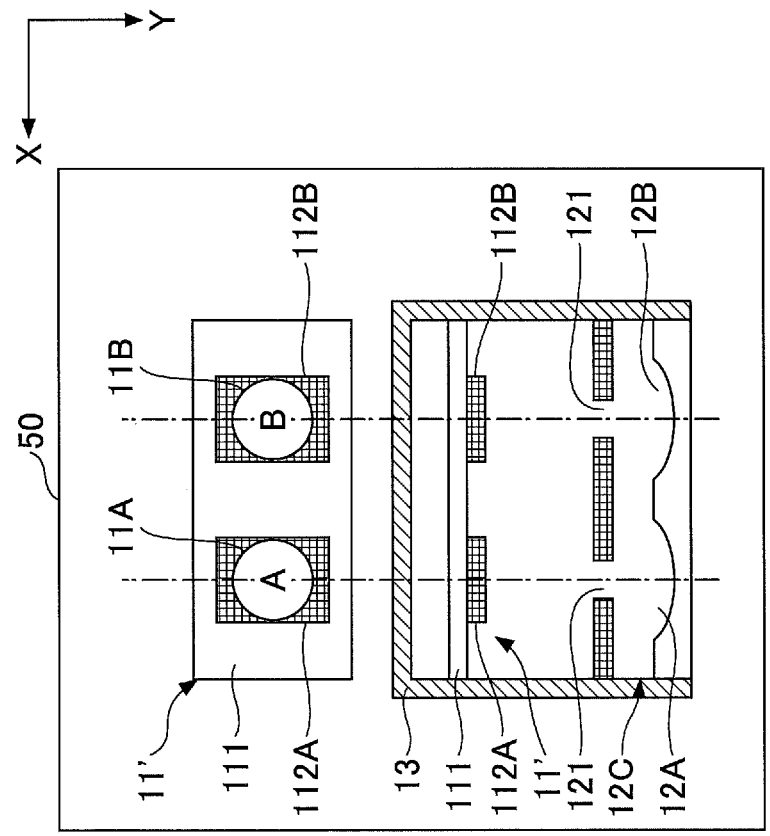

CONVEYED OBJECT DETECTION APPARATUS, CONVEYANCE APPARATUS, AND CONVEYED OBJECT DETECTION METHOD

CROSS-REFERENCE TO APPLICATIONS

The present application claims priority under 35 U.S.C. § 119 to Japanese Patent Application No. 2016-051470, filed Mar. 15, 2016, and Japanese Patent Application No. 2017-034105, filed Feb. 24, 2017. The contents of Japanese Patent Application No. 2016-051470 and Japanese Patent Application No. 2017-034105 are incorporated herein by reference in their entirety.

BACKGROUND

1. Technical Field

The present invention relates a conveyed object detection apparatus, a conveyance apparatus, and a conveyed object detection method.

2. Description of the Related Art

Conventionally, a method of using a head unit and carrying out various processes is known. For example, a method for forming an image in a so-called inkjet method where a print head fires ink is known. Also, a method using such an image forming method to improve printing quality of an image printed on a printing medium is known.

For example, a method of adjusting a position of a print head to improve printing quality is known. In this method, actually, first, positional variations in a lateral direction of a web that is a printing medium passing through a continuous paper printing system are detected by a sensor. Then, in order to cancel the detected positional variations, the position of the print head is adjusted in the lateral direction (for example, see Japanese Laid-Open Patent Application No. 2015-13476).

SUMMARY

A conveyed object detection apparatus according to one aspect includes an optical sensor configured to receive light reflected by a conveyed object; a detection unit configured to use the optical sensor to acquire a detection result indicating a position, a moving speed, or a moved amount of the conveyed object in at least one of a conveyance direction in which the conveyed object is conveyed and a direction perpendicular to the conveyance direction, or a combination of the position, the moving speed, and the moved amount; and a setting unit configured to set an aperture value and an exposure time concerning the optical sensor based on the detection result.

Other objects, features, and advantages will become more apparent from the following detailed description when read in conjunction with the accompanying drawings.

BRIEF DESCRIPTION OF THE DRAWINGS

FIG. 4 is a block diagram illustrating one example of a hardware configuration implementing a detection unit according to the embodiment of the present invention;

FIG. 19 illustrates one example of a position at which a sensor is installed in the apparatus that fires liquid droplets according to the embodiment of the present invention;

FIG. 20 illustrates a hardware configuration of a first comparison example;

FIGS. 28A and 28B generally illustrate a third variant of the hardware configuration of the detection unit according to the embodiment of the present invention;

DETAILED DESCRIPTION OF EMBODIMENTS

Figure 1:
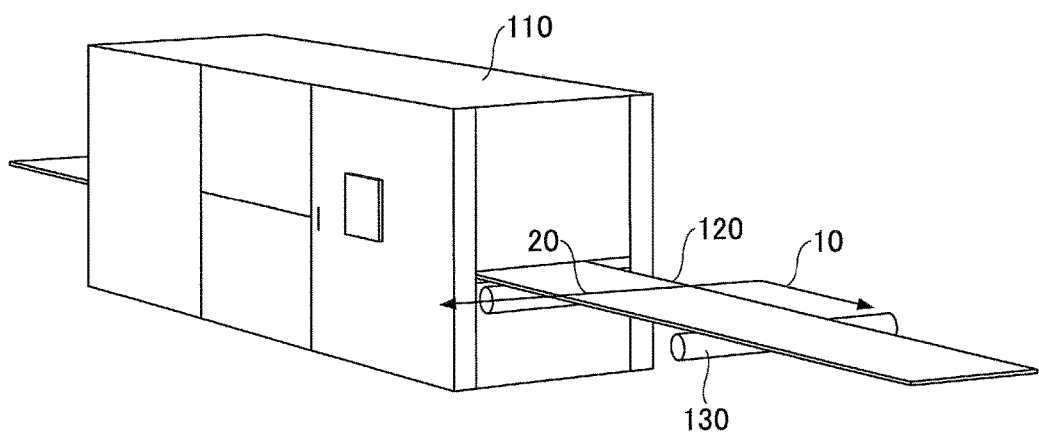
FIG. 1 generally illustrates an apparatus that fires liquid droplets according to an embodiment of the present invention.

In the above-described situation, there is a case where it is demanded to detect landing positions of fired liquid droplets with high accuracy to further the improve image quality of formed images. For example, if the landing position shifts, the image quality may degrade. However, in the conventional art, it may be difficult to detect a position of a conveyed object with high accuracy.

An object of embodiments of the present invention is to provide a conveyed object detection apparatus with which it is possible to detect a position of a conveyed object with high accuracy.

Below, the embodiments of the present invention will be described with reference to the accompanying drawings. Note that, in the specification and the drawings, the same reference numerals are given to elements having substantially the same functional configurations, and duplicate description will be omitted.

Overall Configuration Example

Below, it is assumed that, as one example, a head unit in a conveyance apparatus is a liquid firing head unit that fires liquid droplets.

FIG. 1 generally illustrates an apparatus that fires liquid droplets according to an embodiment of the present invention. For example, the apparatus that fires liquid droplets, as one example of a conveyance apparatus, is an image forming apparatus as illustrated. Liquid droplets fired by the image forming apparatus are recording liquid droplets such as droplets of a water-based or oil-based ink. Below, it is assumed that, as one example, the apparatus that fires liquid droplets is the image forming apparatus 110.

A conveyed object is, for example, a recording medium. In the illustrated example, the image forming apparatus 110 fires liquid droplets onto a web 120 that is one example of a recording medium conveyed by rollers 130 or the like to form an image on the web 120. The web 120 is a so-called continuous paper recording medium, or the like. That is, the web 120 is a roll-shaped sheet that can be wound. Thus, the image forming apparatus 110 is a so-called production-type printer. Below, it is assumed that, as one example, the rollers 130 adjust the tension of the web 120, and the web 120 is conveyed in the illustrated direction (hereinafter, referred to as a "conveyance direction 10"). In FIG. 1, a direction perpendicular to the conveyance direction 10 is referred to as a lateral direction 20. Also, in this example, the image forming apparatus 110 is an inkjet printer that fires four respective inks of black (K), cyan (C), magenta (M), and yellow (Y), in the stated order, to form an image on a certain position of the web 120.

Figure 2:
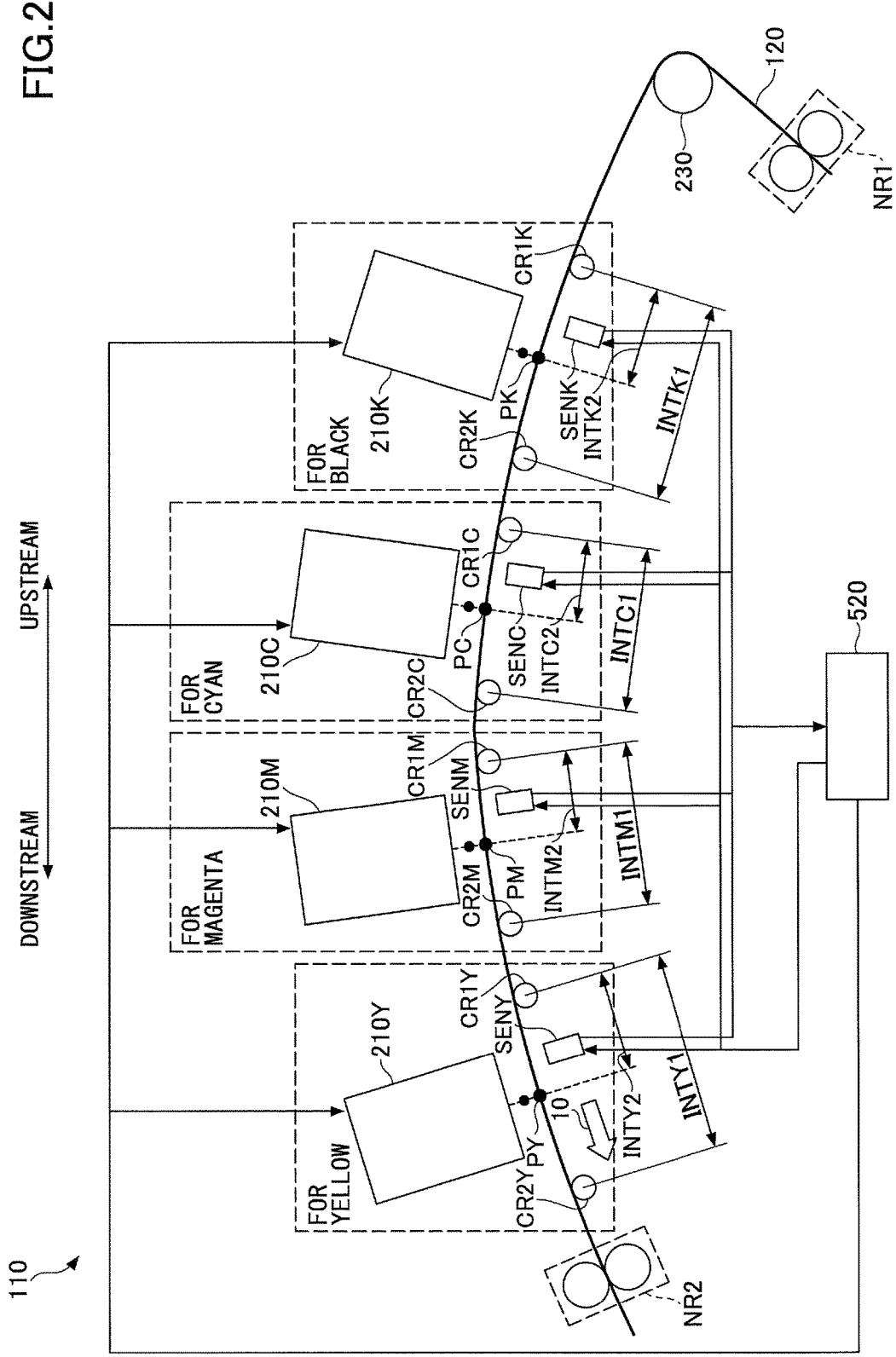
FIG. 2 generally illustrates one example of an overall configuration of the apparatus that fires liquid droplets according to the embodiment of the present invention.

FIG. 2 generally illustrates one example of an overall configuration of the apparatus that fires liquid droplets according to the embodiment of the present invention. As illustrated, the image forming apparatus 110 has four liquid firing head units 210K, 210C, 210M, and 210Y to fire the respective inks of the 4 colors.

Each liquid firing head unit fires liquid droplets of the corresponding color to the web 120 conveyed by in the conveyance direction 10. It is assumed that the web 120 is conveyed by two pairs of nip rollers NR1 and NR2, and a roller 230. The two pairs of nip rollers NR1 and NR2 include a "first nip roller NR1" installed on the upstream side of the respective liquid firing head units 210K-210Y, and a "second nip roller NR2" installed on the downstream side of the respective liquid firing head units 210K-210Y. Note that, the respective nip rollers are rotated while the respective nip rollers NR1 and NR2 sandwich the conveyed object that is the web 120, as illustrated. Thus, the respective nip rollers NR1 and NR2 and the roller 230 act as a mechanism to convey the web 120 in the conveyance direction.

It is desirable that the recording medium that is the web 120 is long. Actually, it is desirable that the length of the recording medium is longer than the distance between the first nip rollers NR1 and the second nip rollers NR2. The recording medium is not limited to a web, and the recording medium may be a folded and stored sheet, i.e., so-called "Z paper", or the like.

Below, in the illustrated overall configuration, the respective liquid firing head units 210K-210Y are installed in the stated order of, from the upstream side through the downstream side, black (K), cyan (C), magenta (M), and yellow (Y). That is, in the example, the liquid firing head unit (hereinafter, referred to as a "black liquid firing head unit 210K") at the most upstream side is the liquid firing head for black (K). The liquid firing head unit (hereinafter, referred to as a "cyan liquid firing head unit 210C") next to the black liquid firing head unit 210K is the liquid firing head for cyan (C). The liquid firing head unit (hereinafter, referred to as a "magenta liquid firing head unit 210M") further next to the cyan liquid firing head unit 210C is the liquid firing head for magenta (M). The liquid firing head unit (hereinafter, referred to as a "yellow liquid firing head unit 210Y") yet further next to the magenta liquid firing head unit 210M is the liquid firing head for yellow (Y).

Each liquid firing head unit fires, based on image data, an ink of the corresponding color at a predetermined position on the web 120. The position from which the ink is fired approximately corresponds to the position (hereinafter, referred to as a "landing position") at which the ink thus fired from the liquid firing head lands on the recording medium, that is, immediately below the liquid firing head. Hereinafter, it is assumed that, as one example, the positions at which the respective liquid firing head units carry out processes are the landing positions.

In this example, a black ink is fired toward the landing position (hereinafter, referred to as a "black landing position PK") of the black liquid firing head unit 210K. In the same way, a cyan ink is fired toward the landing position (hereinafter, referred to as a "cyan landing position PC") of the cyan liquid firing head unit 210C. Also, a magenta ink is fired toward the landing position (hereinafter, referred to as a "magenta landing position PM") of the magenta liquid firing head unit 210M. Also, a yellow ink is fired toward the landing position (hereinafter, referred to as a "yellow landing position PY") of the yellow liquid firing head unit 210Y. Note that, the timing at which each liquid firing head unit fires an ink droplet is controlled by a controller 520 to which the liquid firing head unit is connected.

Also, it is desirable that, for each liquid firing head unit, a plurality of rollers (i.e., CR1K, CR2K, CR1C, CR2C, CR1M, CR2M, CR1Y, and CR2Y) are installed. As illustrated, for example, the rollers are installed on opposite sides of each liquid firing head unit, i.e., on the conveyance-direction upstream side and the conveyance-direction downstream side, respectively. In the illustrated example, for each liquid firing head unit, the roller (hereinafter, referred to as a "first roller") used to convey the web 120 to the corresponding landing position is installed on the upstream side of the liquid firing head unit. For each liquid firing head unit, the roller (hereinafter, referred to as a "second roller") used to convey the web 120 from the corresponding landing position in the downstream direction is installed on the downstream side of the liquid firing head unit.

By thus installing the first and second rollers, respectively, it is possible to reduce flopping of the web 120 at the corresponding landing position. Note that, the first and the second rollers are used to convey the recording medium (i.e., the web 120), and, for example, are driven rollers. Also, the first and second rollers may be driven and rotated by motors, for example.

Note that, the first roller as an example of a first supporting member and the second roller as an example of a second supporting member may be other than rotating bodies such as the driven rollers. That is, the first roller and the second roller may be replaced with any members supporting the conveyed object (i.e., the web 120). For example, the first and second supporting members may be pipes or shafts, each having a circular sectional shape, or the like. Further, the first and second supporting members may be curved plates having curved surfaces at positions touching the conveyed object, or the like. Hereinafter, as one example, it is assumed that the first supporting member is the first roller, and the second supporting member is the second roller.

Actually, in order to fire a black ink toward the black landing position PK, the first roller CR1K for black for conveying the web 120 to the black landing position PK is installed. The second roller CR2K for black for conveying the web 120 in the downstream direction from the black landing position PK is also installed, as mentioned above. In the same way, for the cyan liquid firing head unit 210C, the first roller CR1C for cyan and the second roller CR2C for cyan are installed, respectively. For the magenta liquid firing head unit 210M, the first roller CR1M for magenta and the second roller CR2M for magenta are installed, respectively. For the yellow liquid firing head unit 210Y, the first roller CR1Y for yellow and the second roller CR2Y for yellow are installed, respectively.

Figure 3A:
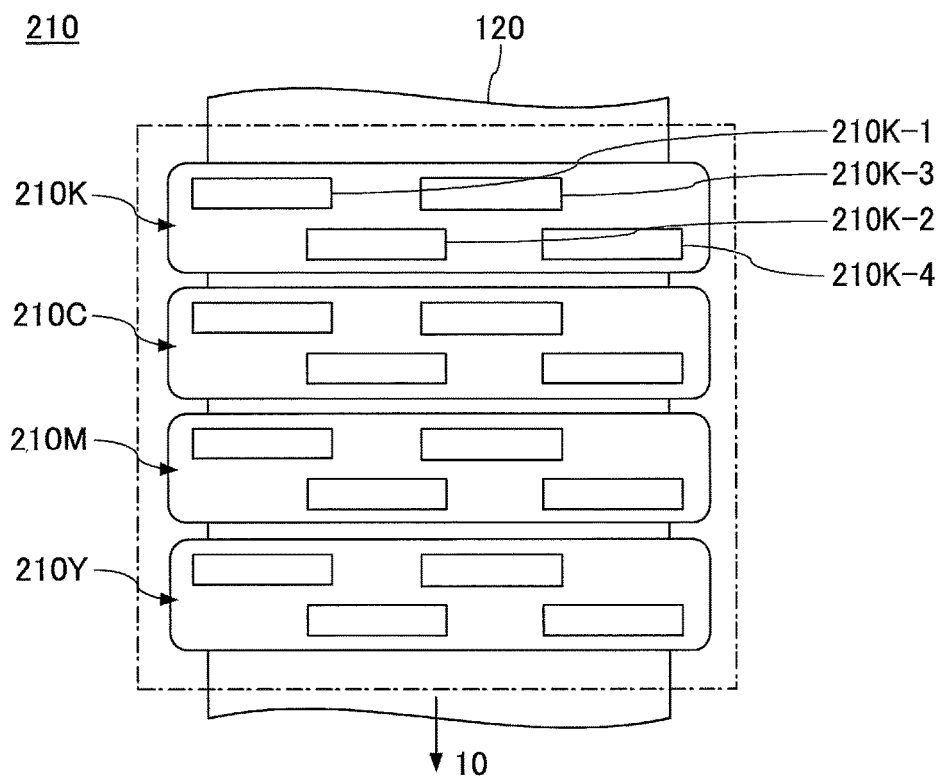
FIGS. 3A and 3B are outline views illustrating one example of an outline shape of a liquid firing head unit according to the embodiment of the present invention.

One example of an outline view of the liquid firing head units 210K-210Y will now be descried using FIG. 3. FIG. 3A is a general plan view of one example of the four liquid firing head units 210K-210Y of the image forming apparatus 110 according to the embodiment of the present invention.

As illustrated in FIG. 3A, the liquid firing head units 210K-210Y are, for example, line-type head units. That is, in the image forming apparatus 110, from the upstream side with respect to the conveyance direction 10, the four liquid firing heads 210K, 210C, 210M, and 210Y are arranged for black (K), cyan (C), magenta (M), and yellow (Y), respectively.

Figure 3B:
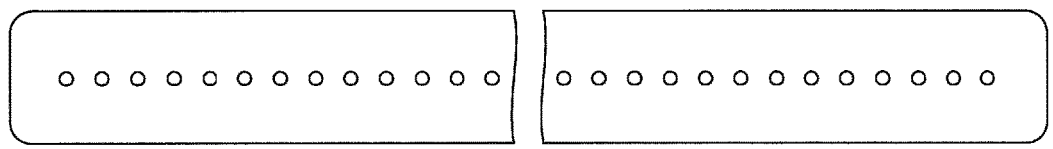

The liquid firing head unit 210K for black (K) has four heads 210K-1, 210K-2, 210K-3, and 210K-4 arranged in a staggering manner, each head extending along the lateral direction. Thus, the image forming apparatus 110 can form an image throughout an image forming area (printing area) of the web 120 in the lateral direction. For example, as illustrated in FIG. 3B, each head, for example, the head 210K-1, has a plurality of nozzles firing black ink droplets. Note that, each of the other liquid firing head units 210C, 210M, and 210Y has the same configuration as the configuration of the liquid firing head unit 210K for black (K), and duplicate description will be omitted.

Note that, in this example, each liquid firing head unit has the four heads, as mentioned above, as one example. It is also possible that each liquid firing head unit has a single head, instead.

Example of Detection Unit

For each liquid firing head unit, a sensor (i.e., SENK, SENC, SENM, or SENY, as illustrated in FIG. 2) is installed as an example of a detection unit for detecting the position of the recording medium in the conveyance direction or the lateral direction. As the sensor, a laser sensor, an air pressure sensor, a photoelectric sensor, an ultrasonic wave sensor, an optical sensor using light such as infrared rays, or the like is used. Note that, the optical sensor may be, for example, a CCD (Charge Coupled Device) camera, a CMOS (Complementary Metal Oxide Semiconductor) camera, or the like.

It is desirable that the optical sensor uses a global shutter. By using a global shutter, in comparison to a rolling shutter, it is possible to reduce a so-called image shift which may occurs when the timing of driving the shutter is shifted, even if the moving speed is high. The detection unit is, for example, a sensor capable of detecting an edge of the recording medium, for example. Also, the detection unit may be implemented by, for example, the following hardware configuration.

FIG. 4 is a block diagram illustrating one example of a hardware configuration implementing the detection unit according to the embodiment of the present invention. For example, as illustrated, the detection unit includes a detection device 50, a control device 52, a storage device 53, and a computing device 54.

First, one example of the detection device 50 will now be described.

Figure 5:
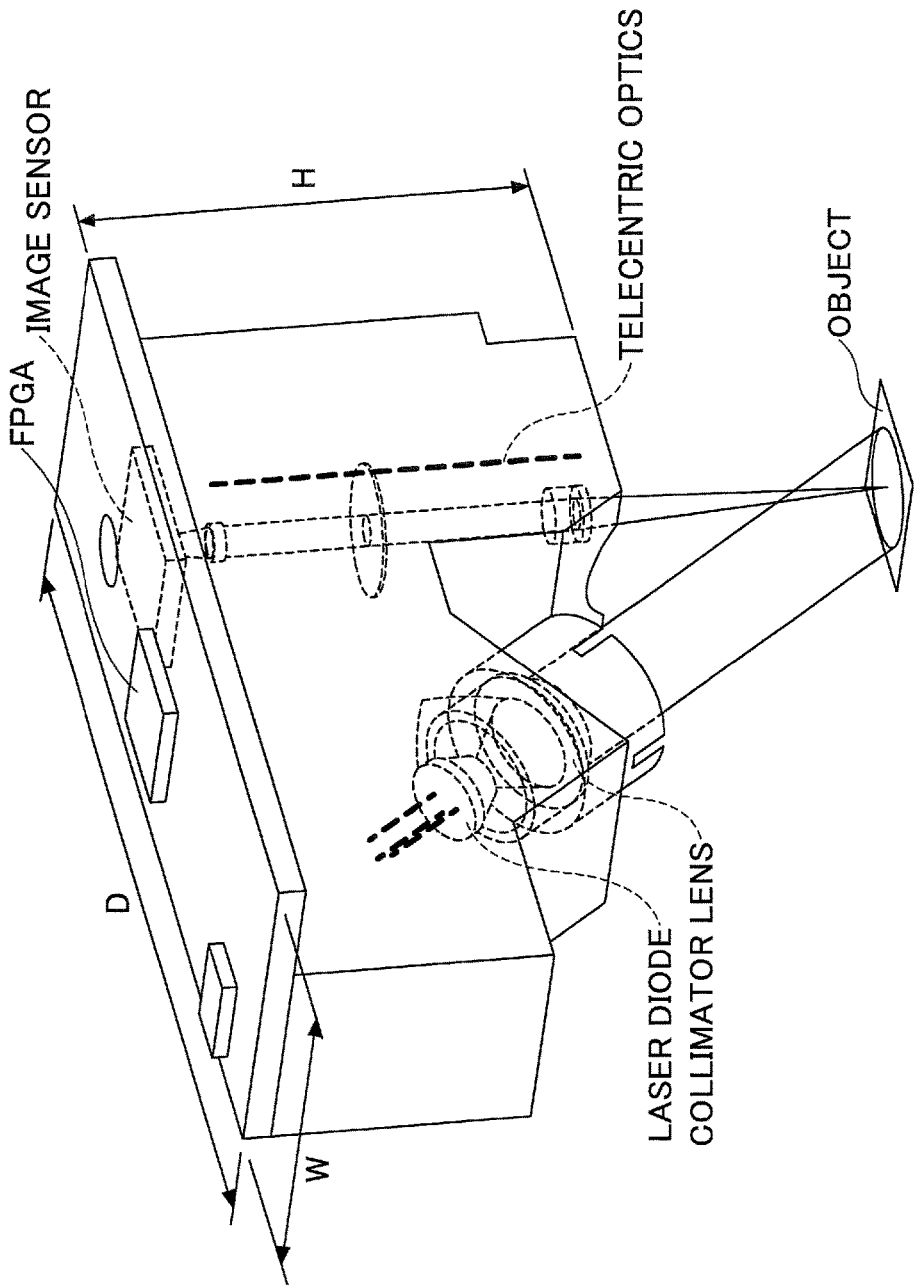
FIG. 5 is an outline view illustrating one example of a detection apparatus according to the embodiment of the present invention.

FIG. 5 includes an outline view illustrating one example of the detection device 50 according to the embodiment of the present invention. The detection unit including the detection device 50 may have the configuration illustrated in FIG. 5.

The illustrated sensor (i.e., the detection device 50) emits illumination light to an object (OBJECT) such as the web 120 to form a speckle pattern. Actually, the sensor includes a semiconductor laser light source (LASER DIODE) and a collimator optical system (COLLIMATOR LENS). In order to take the speckle pattern image, the sensor further includes a CMOS image sensor (IMAGE SENSOR), and a telecentric imaging optical system (TELECENTRIC OPTICS) for converging light to form an image on the CMOS image sensor.

In the illustrated configuration example, the CMOS image sensor takes the speckle pattern image at different times T1 and T2, respectively. Then, using the speckle pattern image taken at the time T1 and the speckle pattern image taken at the time T2, an FPGA circuit (FPGA) carries out cross-correlation calculation. Based on a movement of a correlation peak position calculated from the cross-correlation calculation, the FPGA circuit outputs the moved amount of the object during the time period from the time T1 through the time T2 within the range where images are taken. In the illustrated example, the size of the sensor is 15×60×32 [mm] (width W×depth D×height H).

The CMOS image sensor is one example of an imaging unit, and the FPGA circuit is one example of the computing device 54.

For example, the correlation calculation is carried out as follows.

Correlation Calculation Example

Figure 6:
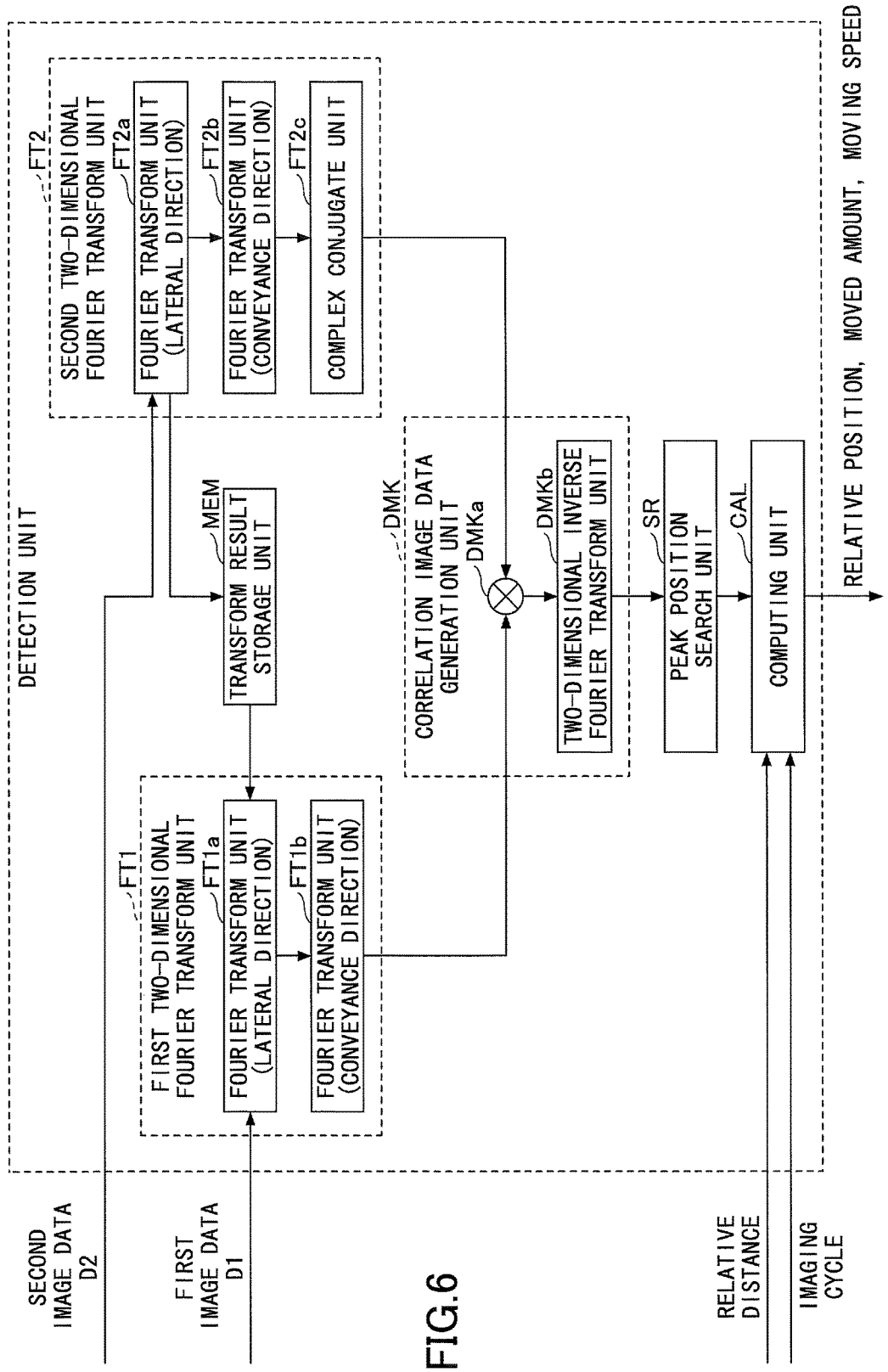
FIG. 6 is a configuration diagram illustrating one example of a correlation calculation method according to the embodiment of the present invention.

FIG. 6 is a configuration diagram illustrating one example of a correlation calculation method according to the embodiment of the present invention. For example, as a result of the detection unit carrying out correlation calculation as illustrated, the detection unit can calculate the relative position, the moved amount, the moving speed, or any combination of the relative position, the moved amount, the moving speed, or the like, of the web 120 at the position of the sensor.

Actually, as illustrated, the detection unit includes a first two-dimensional fourier transform unit FT1, a second two-dimensional fourier transform unit FT2, a correlation image data generation unit DMK, a peak position search unit SR, a computing unit CAL, and a transform result storage unit MEM.

The first two-dimensional fourier transform unit FT1 transforms first image data D1 (that will be described later). The first two-dimensional fourier transform unit FT1 includes a fourier transform unit FT1a for lateral direction and a fourier transform unit FT1b for conveyance direction.

The fourier transform unit FT1a for lateral direction carries out linear Fourier transform on the first image data D1 with respect to the lateral direction. Then, the fourier transform unit FT1b for conveyance direction carries out linear Fourier transform on the first image data D1 with respect to the conveyance direction based on the transform result of the fourier transform unit FT1a for lateral direction. Thus, the fourier transform unit FT1a for lateral direction and the fourier transform unit FT1b for conveyance direction carry out linear Fourier transform with respect to the lateral direction and the conveyance direction, respectively. The first two-dimensional fourier transform unit FT1 outputs the thus calculated transform result to the correlation image data generation unit DMK.

In the same way, the second two-dimensional fourier transform unit FT2 transforms second image data D2 (that will be described later). The second two-dimensional fourier transform unit FT2 includes a fourier transform unit FT2a for lateral direction and a fourier transform unit FT2b for conveyance direction.

The fourier transform unit FT2a for lateral direction carries out linear Fourier transform on the second image data D2 with respect to the lateral direction. Then, the fourier transform unit FT2b for conveyance direction carries out linear Fourier transform on the second image data D2 with respect to the conveyance direction based on the transform result of the fourier transform unit FT2a for lateral direction. Thus, the fourier transform unit FT2a for lateral direction and the fourier transform unit FT2b for conveyance direction carry out linear Fourier transform with respect to the lateral direction and the conveyance direction, respectively.

Next, a complex conjugate unit FT2c in the second two-dimensional fourier transform unit FT2 calculates the complex conjugate of the transform result of the fourier transform unit FT2a for lateral direction and the fourier transform unit FT2b for conveyance direction. Then, the second two-dimensional fourier transform unit FT2 outputs the complex conjugate calculated by the complex conjugate unit FT2c to the correlation image data generation unit DMK.

Next, the correlation image data generation unit DMK generates correlation image data based on the transform result of the first image data D1, output from the first two-dimensional fourier transform unit FT1, and the transform result of the second image data D2, output from the second two-dimensional fourier transform unit FT2.

The correlation image data generation unit DMK includes an adding-up unit DMKa and a two-dimensional inverse fourier transform unit DMKb.

The adding-up unit DMKa adds up the transform result of the first image data D1 and the transform result of the second image data D2. Then, the adding-up unit DMKa outputs the adding-up result to the two-dimensional inverse fourier transform unit DMKb.

The two-dimensional inverse fourier transform unit DMKb carries out two-dimensional inverse fourier transform on the adding-up result of the adding-up unit DMKa. As a result of the two-dimensional inverse fourier transform being thus carried out, the correlation image data is generated. Then, the two-dimensional inverse fourier transform unit DMKb outputs the correlation image data to the peak position search unit SR.

The peak position search unit SR searches the generated correlation image data for a peak position at which the data has a steepest value (that is, the rises up steeply), i.e., peak brightness (a peak value) is present. First, as the correlation image data, the light intensity, that is, the values indicating the magnitudes of brightness (i.e., brightness values) are input. The brightness values are input in a form of a matrix.

In the correlation image data, the brightness values are arranged at a pixel pitch interval of an area sensor, that is, at a pixel size interval. Therefore, it is desirable that the search for the peak position is carried out in such a way that, after so-called subpixel processing is carried out, the search is carried out. Through the subpixel processing, the peak position can be searched for with high accuracy. Therefore, the detection unit can output the position, the moved amount, the moving speed, and so forth, with high accuracy.

For example, the search by the peak position search unit SR is carried out, as follows.

Figure 7:
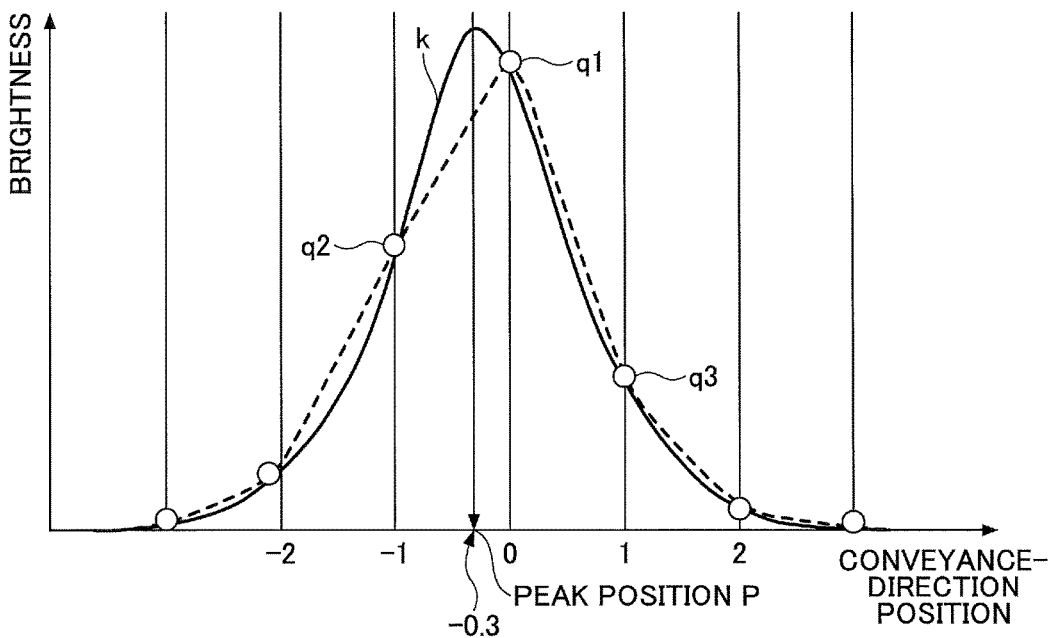
FIG. 7 illustrates one example of a peak position search method in correlation calculation according to the embodiment of the present invention.

FIG. 7 illustrates one example of a peak position search method in the correlation calculation according to the embodiment of the present invention. In FIG. 7, the horizontal axis denotes the position in the conveyance direction in the image indicated by the correlation image data. The vertical axis denotes the brightness of the image indicated by the correlation image data.

Below, three pieces of data, i.e., a first data value q1, a second data value q2, and a third data value q3, from among the brightness values indicated by the correlation image data, will be described, for example. That is, in this example, the peak position search unit SR (FIG. 6) searches for the peak position P from the curve k connecting the first data value q1, the second data value q2, and the third data value q3.

First, the peak position search unit SR calculates the respective differences between the brightness values of the image indicated by the correlation image data. Then, the peak position search unit SR extracts the combination of the data values having the greatest difference from among the calculated differences. Next, the peak position search unit SR extracts the combinations of data values adjacent to the combination of the data values having the greatest difference. Thus, the peak position search unit SR can extract the three data values, i.e., the first data value q1, the second data value q2, and the third data value q3, as illustrated. Then, by calculating the curve k connecting the extracted three data values, the peak position search unit SR can acquire the peak position P to be searched for. Thus, the peak position search unit SR can search for the peak position P more rapidly while the calculation amount of the subpixel processing, or the like, can be reduced. Note that, the position of the combination of the data values having the greatest difference is the steepest position. Also, the subpixel processing can be replaced with other processing than the processing mentioned above.

As a result of the peak position search unit SR searching for the peak position, the following calculation result, for example, can be acquired.

Figure 8:
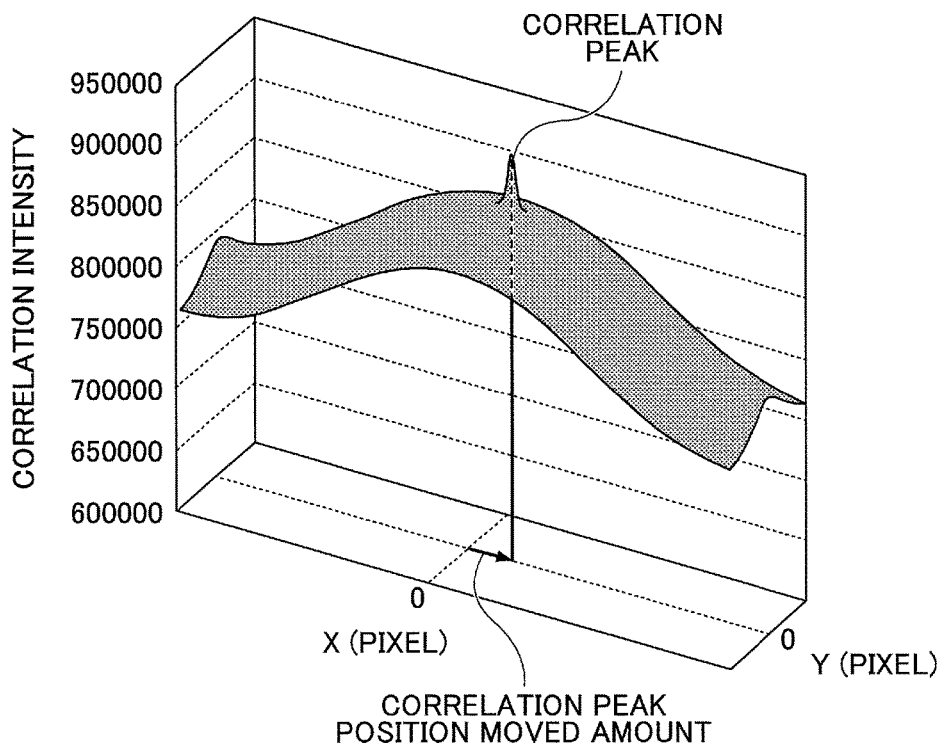
FIG. 8 illustrates a calculation result example of correlation calculation according to the embodiment of the present invention.

FIG. 8 illustrates a calculation result example of the correlation calculation according to the embodiment of the present invention. FIG. 8 illustrates a correlation intensity distribution of a cross-correlation function. In FIG. 8, X-axis and Y-axis denote serial numbers of pixels. The peak position such as a "correlation peak" illustrated is searched for by the peak position search unit SR (see FIG. 6).

Returning to FIG. 6, a computing unit CAL calculates the relative position, moved amount, moving speed, or the like, of the web 120. For example, the computing unit CAL can calculate the relative position and the moved amount by calculating the difference between the center position in the correlation image data and the peak position searched for by the peak position search unit SR.

Also, the computing unit CAL can calculate the moving speed by dividing the moved amount by the elapsed time.

Thus, the detection unit can detect the relative position, the moved amount, the moving speed, or the like, through the correlation calculation. Note that, the actual method to detect the relative position, the moved amount, the moving speed, or the like, is not limited to the above-mentioned method. For example, the detection unit may detect the relative position, the moved amount, the moving speed, or the like, as follows.

First, the detection unit binarizes the brightness values of the first image data D1 and the second image data D2. That is, the detection unit acquires the value "0" if the brightness value is less than or equal to a certain threshold, whereas the detection unit acquires the value "1" if the brightness value is greater than the certain threshold. The detection unit may detect the relative position by comparing the thus binarised first image data and second image data.

The detection unit may detect the relative position, the moved amount, the moving speed, or the like, using a yet another method. For example, the detection unit may carry out pattern matching processing to detect the relative position using respective patterns appearing in the respective sets of image data.

Note that the example where positional variations occur in the Y direction has been described. However, the peak position is shifted also in the X direction if a positional variation occurs in the X direction.

Returning to FIG. 4, the control device 52 controls the detection device 50, and so forth. Actually, for example, the control device 52 outputs a trigger signal to the detection device 50, to control the timing to drive the shutter in the CMOS image sensor, for example. Also, the control device 52 controls the detection device 50 to acquire a two-dimensional image. Then, the control device 52 sends the two-dimensional image taken by the detection device 50 to the storage device 53, and so forth.

The storage device 53 is a so-called memory, or the like. Note that, it is desirable that the storage device 53 is such that the two-dimensional image given by the control device 52 or the like is divided, and the divisions are stored in different storage areas, respectively.

The computing device 54 is a microcomputer, or the like. That is, the computing device 54 carries out calculation to implement various sorts of processing using the image data stored in the storage device 53, and so forth.

Each of the control device 52 and the computing device 54 is, for example, a CPU (Central Processing Unit), an electronic circuit, or the like. Note that, two or more of the control device 52, the storage device 53, and the computing device 54 may be included in a single unit. For example, the control device 52 and the computing device 54 may be implemented by a single CPU, or the like.

Figure 9:
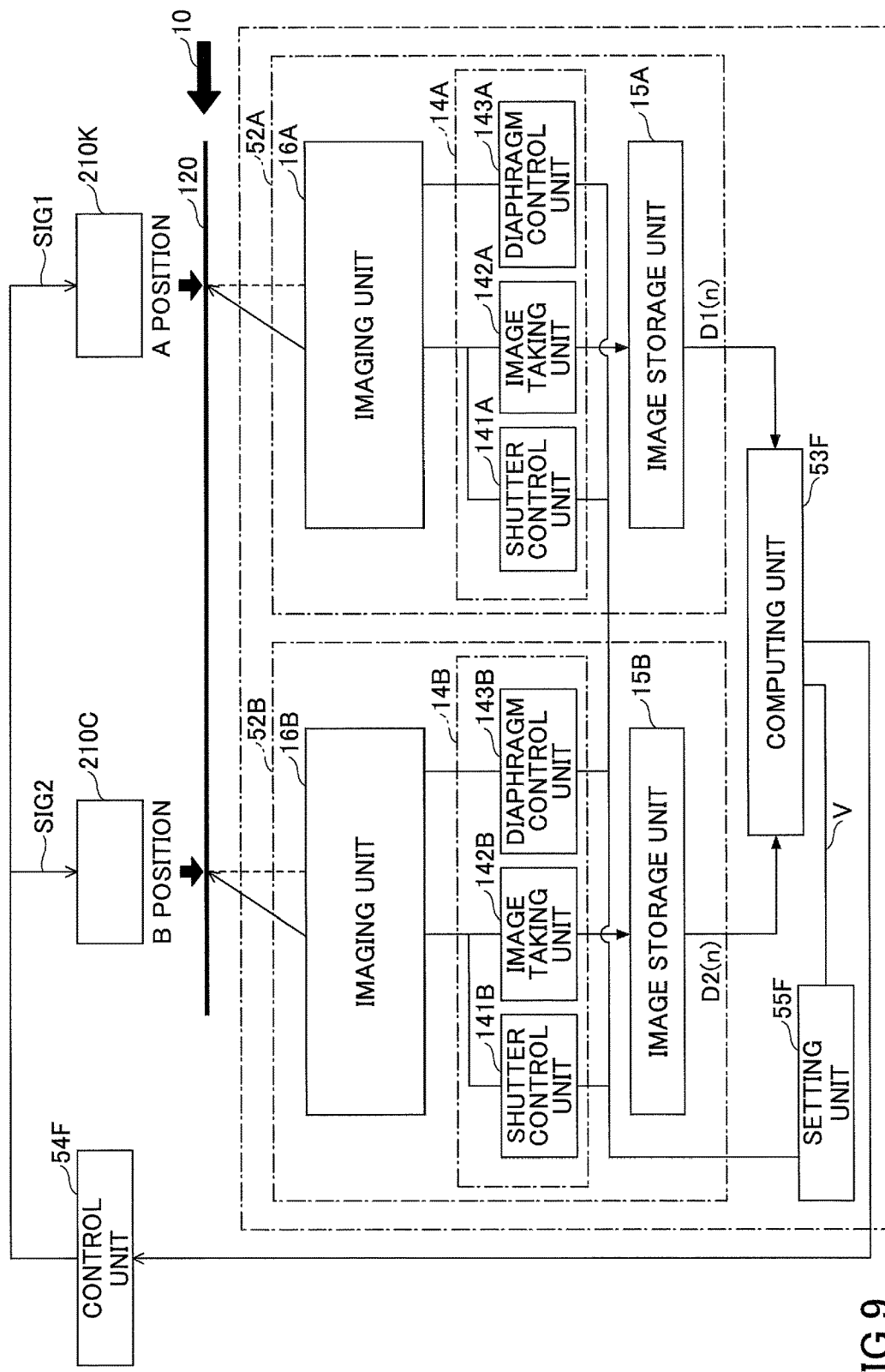
FIG. 9 is a function block diagram illustrating one example of a functional configuration for using the detection unit according to the embodiment of the present invention.

FIG. 9 is a functional block diagram illustrating one example of a functional configuration for using the detection unit according to the embodiment of the present invention. Below, from among the detection units provided for the respective liquid firing head units 210K-210Y, a combination of the black liquid firing head unit 210K and the cyan liquid firing head unit 210C will be described, as one example, as illustrated.

Also, below, it is assumed that, as one example, the detection unit 52A for the black liquid firing head unit 210K outputs a detection result concerning an "A position", and the detection unit 52B for the cyan liquid firing head unit 210C outputs a detection result concerning a "B position". The detection unit 52A for the black liquid firing head unit 210K includes, for example, an imaging unit 16A, an imaging control unit 14A, and an image storage unit 15A. In this example, the detection unit 52B for the cyan liquid firing head unit 210C has, for example, the same configuration as the detection unit 52A, and includes an imaging unit 16B, an imaging control unit 14B, and an image storage unit 15B. Therefore, below, the detection unit 52A will be described, as one example.

The imaging unit 16A takes an image of the web 120 conveyed in the conveyance direction 10, as illustrated. Note that, the imaging unit 16A is implemented by, for example, the detection device 50, and so forth (see FIG. 4, and so forth).

The imaging control unit 14A includes a shutter control unit 141A and an image taking unit 142A. The imaging control unit 14A is implemented by, for example, the control device 52, and so forth (see FIG. 4).

The image taking unit 142A acquires the image taken by the imaging unit 16A.

The shutter control unit 141A controls the timing of taking the image by the imaging unit 16A.

The image storage unit 15A stores the image acquired by the imaging control unit 14A. The image storage unit 15A is implemented by, for example, the storage device 53, and so forth (see FIG. 4).

The computing unit 53F can calculate, based on the images stored in the image storage units 15A and 15B, the position of a pattern that the web 120 has, the moving speed at which the web 120 is conveyed, and the moved amount for which the web 120 has been conveyed. The computing unit 53F outputs, to the shutter control unit 141A, time difference data $\Delta t$ indicating the timing of driving the shutter. That is, the computing unit 53F sends information of the timing of driving the shutter to the shutter control unit 141A such that the image at the "A position" and the image at the "B position" will be taken with the time difference $\Delta t$ therebetween. Also, the computing unit 53F may control a motor or the like conveying the web 120 in such a manner that the calculated moving speed will be acquired. Note that, the computing unit 53F is implemented by, for example, the controller 520, and so forth (see FIG. 2).

The web 120 is a member having scattering property on the surface or in the inside. Therefore, if the web 120 is irradiated with laser light, the reflected light reflects in a diffused reflection manner. Due to the defused reflection, a pattern appears on the web 120. The pattern is a spot called a "speckle", i.e., so-called a speckle pattern. Therefore, when an image of the web 120 is taken, the image where a speckle pattern appears is acquired. Because the position of the speckle pattern in the image can be detected, it is possible to detect where a predetermined position in the web 120 is present. Note that, the speckle pattern is generated because, due to unevenness present on the surface or in the inside of the web 120, laser light with which the web 120 is irradiated has interference.

The light source is not limited to a device using laser light. For example, the light source may be a LED (Light Emitting Diode), an EL (Electro-Luminescence), or the like. Depending on the actual type of the light source, the pattern is not limited to the speckle pattern. Below, it is assumed that the pattern is the speckle pattern.

Therefore, as the web 120 is conveyed, the speckle pattern of the web 120 is also conveyed together. Therefore, as a result of detecting the same speckle pattern at different times, respectively, the moved amount of the web 120 can be carried. That is, by acquiring the moved amount by thus detecting the speckle pattern, the computing unit 53F can acquire the moved amount of the web 120. By converting the moved amount into the amount per unit time, the computing unit 53F can acquire the moving speed at which the web 120 is conveyed.

Actually, the relationships of the following Formula (1) hold, where V denotes the moving speed [mm/s] and L denotes the relative distance [mm] which is the distance between the sensors in the conveyance direction 10.

$$\Delta t = L/V \quad (1)$$

There, the relative distance L [mm] is the space between the "A position" and the "B position" illustrated in FIG. 9, and therefore, can be previously acquired. Therefore, by thus detecting the time difference Δt between the difference times, the computing unit 53F can acquire the moving speed V [mm/s] from Formula (1). Thus, based on the speckle pattern, the image forming apparatus can acquire, with high accuracy, the position, the moved amount, or the moving speed of the web 120, or any combinations of the position, the moved amount, and the moving speed. Note that the image forming apparatus may output a combination of any one or more of the position, the moved amount, and the moving speed of the web 120 in the conveyance direction.

As illustrated in FIG. 9, the positions at which the imaging units 16A and 16B take images have the fixed space in the conveyance direction 10. Each imaging unit takes an image of the web 120 at the corresponding position. Thus, based on the speckle pattern, the image forming apparatus can acquire a detection result indicating the position of the web 120 in the conveyance direction or the direction (i.e., the lateral direction) perpendicular to the conveyance direction with high accuracy.

The detection result may also indicate the relative position. The relative position indicates the difference between the position detected by any sensor and the position detected by another sensor. Other than this method, the same sensor may take images a plurality of times, and the relative position may be the difference between the positions in the corresponding images. That is, for example, the relative position may be the difference between the position detected from one frame and the position detected from the subsequent frame. Thus, the relative position indicates the shift amount of the position with respect to the position detected from the previous frame or by the other sensor.

Note that, each sensor may also detect the position in the lateral directions, or the like. Each sensor may also be used to detect the position in each of both the conveyance direction and the lateral directions. By using each sensor to detect the position concerning both conveyance direction and the lateral directions, it is possible to reduce the cost for both the conveyance direction and lateral directions. Then, the number of the sensors can be reduced, and therefore, the spaces for installing the sensors can also be reduced.

Also, the computing unit 53F carries out the cross-correlation calculation on the first image data D1(n) and the second image data D2(n) representing images taken by the detection units 52A, and 52B, respectively. Note that the image generated through the cross-correlation calculation is referred to as the "correlation image". For example, the computing unit 53F calculates a shift amount ΔD(n) based on the correlation image.

For example, the cross-correlation calculation is calculation illustrated in the following Formula (2).

$$D1 \star D2^* = F-1[F[D1] \cdot F[D2]^*] \quad (2)$$

In Formula (2), "D1" denotes the first image data D1(n), that is, image data representing an image taken at the "A position". "D2" denotes the first image data D2(n), that is, image data representing an image taken at the "B position". "F[ ]" denotes Fourier transform, and "F−1[ ]" denotes inverse Fourier transform. "*" denotes the complex conjugate, and "★" denotes the cross-correlation calculation.

As illustrated in Formula (2), through the cross-correlation calculation "D1★D2" between the first image data D1 and the second image data D2, the correlation image data representing the correlation image can be acquired. If the first image data D1 and the second image data D2 are two-dimensional image data, the correlation image data also representing the two-dimensional image data. If the first image data D1 and the second image data D2 are one-dimensional image data, the correlation image data indicating the correlation image is also one-dimensional image data.

Note that, if, concerning the correlation image, for example, a broad brightness distribution will be considered, a phase restriction correlation method may be used. The phase restriction correlation method uses, for example, calculation illustrated in the following Formula (3).

$$D1 \star D2^* = F-1[P[F[D1]] \cdot P[F[D2]^*]] \quad (3)$$

In Formula (3), "P[ ]" denotes extracting phase information. Note that, the amplitude is assumed as "1".

Thus, the computing unit 53F can calculate the shift amount ΔD(n) based on the correlation image even considering a broad brightness distribution.

The correlation image indicates correlation relationships between the first image data D1 and the second image data D2. Actually, the greater the degree of coincidence between the first image data D1 and the second image data D2 becomes, the nearer the brightness output has a steep peak (i.e., so called a correlation peak) to the center of the correlation image. If the first image data D1 coincides with the second image data D2, the center of the correlation image is the same as the position of the peak.

Based on the timings calculated through the calculation, the black liquid firing head unit 210K and the cyan liquid firing head unit 210C fire liquid droplets, respectively. Note that, the timings of firing liquid droplets are controlled by a first signal SIG1 for the black liquid firing head unit 210K and a second signal SIG2 for the cyan liquid firing head unit 210C, these signals being output by the controller 520, or the like. As illustrated, based on the calculation result of the computing unit 53F, a control unit 54F outputs the signals to control the timings. Note that, the control unit 54F is implemented by, for example, the controller 520, and so forth.

Also, the computing unit 53F outputs the moving speed V calculated from the detection result to the setting unit 55F. Then, based on the moving speed V received from an external unit such as the computing unit 53F, the setting unit 55F calculates the aperture value, the exposure time, or both. It is also possible that, to the setting unit 55F, the moving speed V is input based on an operation mode such as a resolution of an output image in the image forming apparatus. Note that, the setting unit 55F is implemented by, for example, the control device 52 (see FIG. 4), and so forth.

The setting unit 55F reduces the exposure time and reduces the aperture value if the moving speed V is high. On the other hand, the setting unit 55F increases the exposure time and increases the aperture value if the moving speed V is low.

Then, diaphragm control units 143A and 143B (see FIG. 9) control the diaphragms in such a manner that the aperture values that are set by the setting unit 55F will be acquired. Note that, the diaphragm control units 143A and 143B are implemented by, for example, the control device 52 (see FIG. 4), an actuator ACA (see FIG. 16), and so forth.

In the same way, the shutter control units 141A and 141B control the shutter speeds, or the like, in such a manner that the exposure times that are set by the setting unit 55F will be acquired.

Thus, each detection unit can take an image of the web 120 based on the exposure time and the aperture value suitable to the moving speed V of the web 120. Note that the calculations and the settings may also be carried out by the controller 520, or the like.

Returning to FIG. 2, hereinafter, the sensor provided for the black liquid firing head unit 210K will be referred to as a "sensor SENK for black". The sensor provided for the cyan liquid firing head unit 210C will be referred to as a "sensor SENC for cyan". The sensor provided for the magenta liquid firing head unit 210M will be referred to as a "sensor SENM for magenta". The sensor provided for the yellow liquid firing head unit 210Y will be referred to as a "sensor SENY for yellow". Also, hereinafter, the sensor SENK for black, the sensor SENC for cyan, the sensor SENM for magenta, and the sensor SENY for yellow may be generally referred to as simply "sensors".

Also, below, "the position at which the sensor is installed" indicates a position at which detection and so forth is carried out. Therefore, it is possible that the devices for carrying out detection and so forth are not installed at "the position at which the sensor is installed", and the devices other than the sensor may be installed at other positions, and may be connected via cables or the like. Note that, the sensor SENK for black, the sensor SENC for cyan, the sensor SENM for magenta, and the sensor SENY for yellow, illustrated in FIG. 2, are examples indicating the positions at which the sensors are installed.

Thus, it is desirable that the position where the corresponding sensor is installed is close to each landing position.

As a result of the corresponding sensor being installed at a position near each landing position, the distance between each landing position and the corresponding sensor becomes smaller. As a result of the distance between each landing position and the corresponding sensor becoming smaller, the detection error can be reduced. Therefore, the image forming apparatus can detect the position of the recording medium with high accuracy in the conveyance direction or the lateral direction perpendicular to the conveyance direction through the sensor.

The position close to each landing position is, actually, a position between the corresponding first and second rollers. That is, in the illustrated example, it is desirable that the position at which the sensor SENK for black is installed is, as illustrated, in an interval INTK1 between the rollers for black. In the same way, it is desirable that the position at which the sensor SENC for cyan is installed is, as illustrated, in an interval INTC1 between the rollers for cyan. Also, it is desirable that the position at which the sensor SENM for magenta is installed is, as illustrated, in an interval INTM1 between the rollers for magenta. Also, it is desirable that the position at which the sensor SENY for yellow is installed is, as illustrated, in an interval INTY1 between the rollers for yellow. As a result of the sensors being thus installed between the corresponding rollers, the sensors can detect the position of the recording medium, or the like, at the positions close to the respective landing positions. Also, in many cases, the moving speed is relatively stable between the rollers. Therefore, the image forming apparatus can detect the position of the recording medium in the conveyance direction or the lateral direction perpendicular to the conveyance direction with high accuracy.

It is desirable that, the position at which each sensor is installed is near the first roller than the landing position, between the corresponding rollers. That is, it is desirable that the corresponding sensor is installed on the upstream side of each landing position.

Actually, the position at which the sensor SENK for black is installed falls within the interval from the black landing position PK through the position at which the first roller CR1K for black is installed (hereinafter, referred to as an "upstream interval INTK2 for black") in the upstream direction. In the same way, it is desirable that the position where the sensor SENC for cyan is installed falls within the interval from the cyan landing position PC through the position at which the first roller CR1C for cyan is installed (hereinafter, referred to as an "upstream interval INTC2 for cyan") in the upstream direction. In the same way, it is desirable that the position where the sensor SENM for magenta is installed falls within the interval from the magenta landing position PM through the position at which the first roller CR1M for magenta is installed (hereinafter, referred to as an "upstream interval INTM2 for magenta") in the upstream direction. In the same way, it is desirable that the position where the sensor SENY for yellow is installed falls within the interval from the yellow landing position PY through the position at which the first roller CR1Y for yellow is installed (hereinafter, referred to as an "upstream interval INTY2 for yellow") in the upstream direction.

After the sensors are installed in the upstream interval INTK2 for black, the upstream interval INTC2 for cyan, the upstream interval INTM2 for magenta, and the upstream interval INTY2 for yellow, respectively, the image forming apparatus can detect the position of the recording medium in the conveyance direction or the lateral direction perpendicular to the conveyance direction with high accuracy. Also, as a result of the sensors being installed at these positions, the corresponding sensor is installed on the upstream side of each landing position. Therefore, the image forming apparatus can first detect the position of the recording medium in the conveyance direction or the lateral direction perpendicular to the conveyance direction with high accuracy on the upstream side by the sensor, and can calculate the timing at which each liquid firing head unit fires ink droplets. That is, after the web 120 is conveyed during the calculation, each liquid firing head unit can then fire ink droplets at the calculated timing.

Note that, if the corresponding sensor were installed immediately below each liquid firing head unit, a color shift may occur depending on a delay of control operation, or the like. Therefore, by installing the corresponding sensor on the upstream side of each landing position, the image forming apparatus can reduce a color shift, and improve the image quality. There may be a restriction to install the corresponding sensor near each landing position. Therefore, it is desirable to install the corresponding sensor at a position nearer to each first roller than each landing position.

Also, the corresponding sensor may be installed, for example, immediately below each liquid firing head unit. Below, it is assumed that the corresponding sensor is installed immediately below each liquid firing head unit, as one example. As a result of, as in the example, the sensor being immediately below, the accurate moved amount immediately below can be detected by the sensor. Therefore, if it is possible to carry out a control operation at a high speed, it is desirable that the corresponding sensor is installed at a position nearer to immediately below each liquid firing head unit. On the other hand, it is also possible that the corresponding sensor is not installed immediately below each liquid firing head unit. If the corresponding sensor is not installed immediately below each liquid firing head unit, the calculation is carried out in the same way.

Also, if an error is tolerable, the corresponding sensor may be installed immediately below each liquid firing head unit, or on the downstream side of immediately below each liquid firing head unit between the corresponding first and second rollers.

Also, the image forming apparatus may further include a measurement unit such as an encoder. Below, it is assumed that, as one example, the measurement unit is implemented by an encoder. Actually, an encoder is installed, for example, to the axis of rotation of the roller 230. Thus, it is possible to measure the moved amount in the conveyance direction based on the rotation amount of the roller 230. By using the measurement result together with the detection result of the sensors, the image forming apparatus can fire liquid droplets to the web 120 with higher accuracy.

Figure 10A:
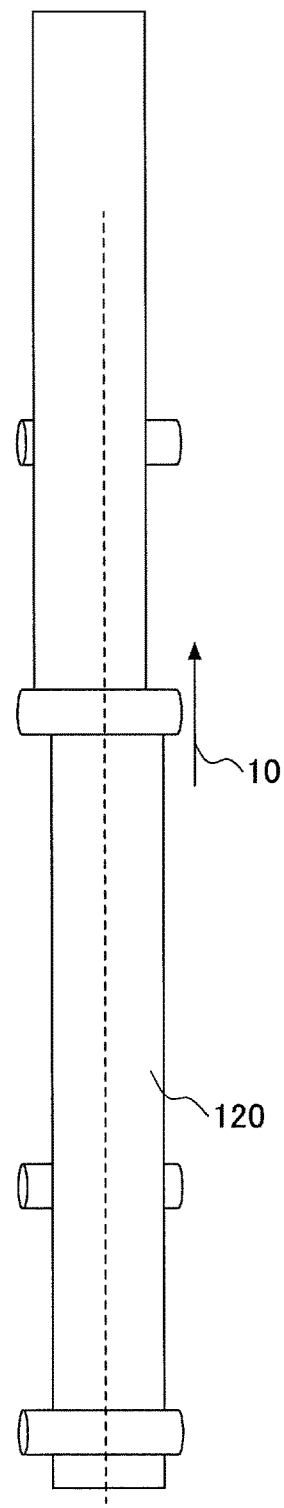
FIGS. 10A and 10B illustrate an example where the position of a recording medium varies in lateral directions.
Figure 10B:
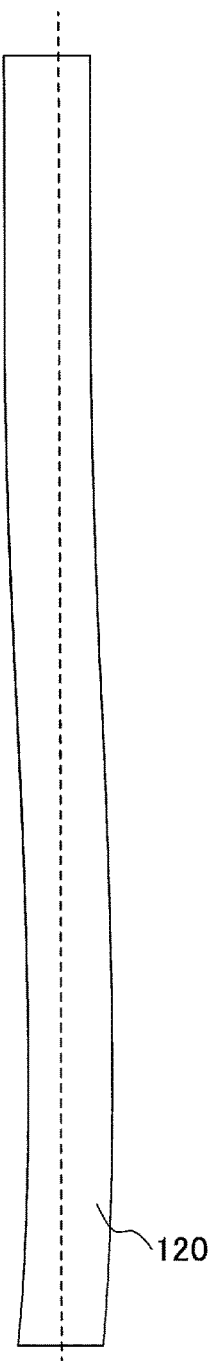

FIGS. 10A and 10B illustrate an example where the position of the recording medium varies in the lateral directions. Below, it is assumed that, as illustrated in FIG. 10A, the web 120 is conveyed in the conveyance direction 10 (in FIG. 10A, the web 120 is conveyed upward). As illustrated, the web 120 is conveyed by rollers, or the like. Thus, while the web 120 is conveyed, the web 120 may vary in position in the lateral directions as illustrated in FIG. 10B, for example. That is, the web 120 may run meandering as illustrated in FIG. 10B.

Positional variation of the web 120 in the lateral directions, that is, "meandering", occurs, for example, due to eccentricity, misalignment, or the like, of the conveyance rollers, a severance of the web 120 with a blade, or the like. Also, if the web 120 has the width smaller in the lateral directions, or the like, heat expansion of the rollers may adversely affect the position of the web 120 in the lateral directions.

Figure 11:
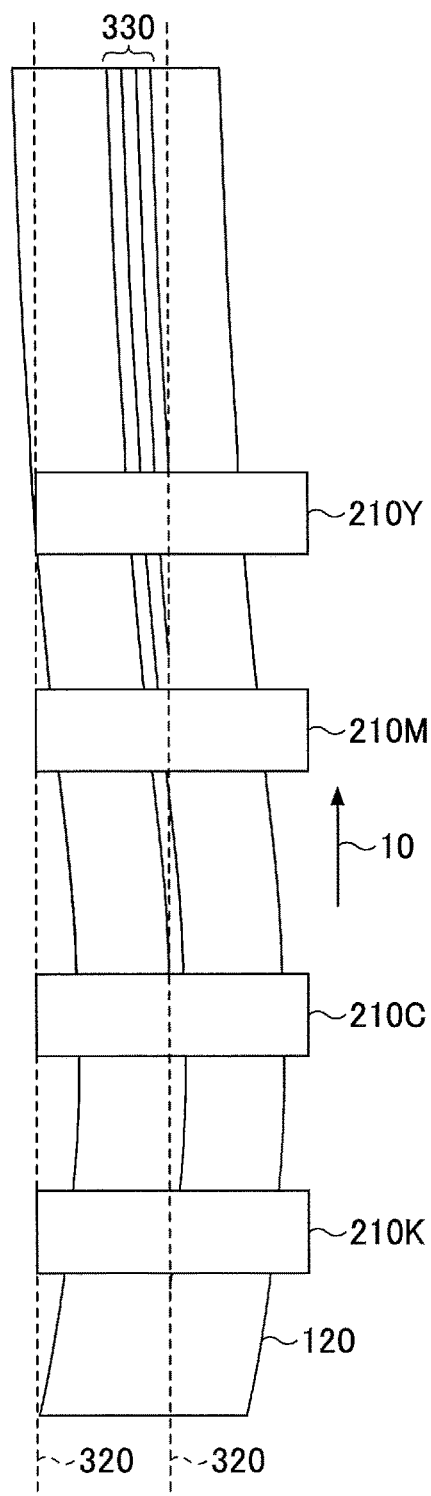
FIG. 11 illustrates one example of a cause of a color shift.

FIG. 11 illustrates one example of a cause of a color shift. If the position of the recording medium varies in the lateral directions as illustrated in FIGS. 10A and 10B, that is, "meandering", occurs, a color shift may likely to occur as will be described with reference to FIG. 11.

Actually, if a plurality of colors are used to form an image on the recording medium, that is, if a color image is formed, as illustrated, the image forming apparatus forms a color image on the web 120 through so-called color planes, i.e., by superposing inks of respective colors fired by corresponding liquid firing head units.

If the lateral position variations illustrated with FIGS. 10A and 10B occur, "meandering" may occur with respect to, for example, reference lines 320. In this case, if the respective liquid firing head units fire the respective inks at the same positions, a color shift 330 may occur because the web 120 varies in position laterally between the respective liquid firing head units 210K-210Y due to "meandering". That is, the color shift 330 occurs because lines or the like formed by the inks fired by the respective liquid firing head units 210K-210Y have their positions shifted thereamong. If such a color shift 330 occurs, the image quality of the image formed on the web 120 may degrade.

Example of Control Unit

The controller 520 (see FIG. 2) that is one example of a control unit will now be described.

Note that, as can be seen from FIGS. 2, 12, and 14, described below, the apparatus that fires liquid droplets illustrated in FIG. 2 and so forth and described above, except the controller 520 illustrated in FIG. 2, is included in an image output device 72Ei. In other words, FIG. 12 also illustrates the apparatus that fires liquid droplets illustrated in FIG. 2 and so forth and described above in such a manner that the control unit (i.e., the controller 520) is illustrated in detail.

Figure 12:
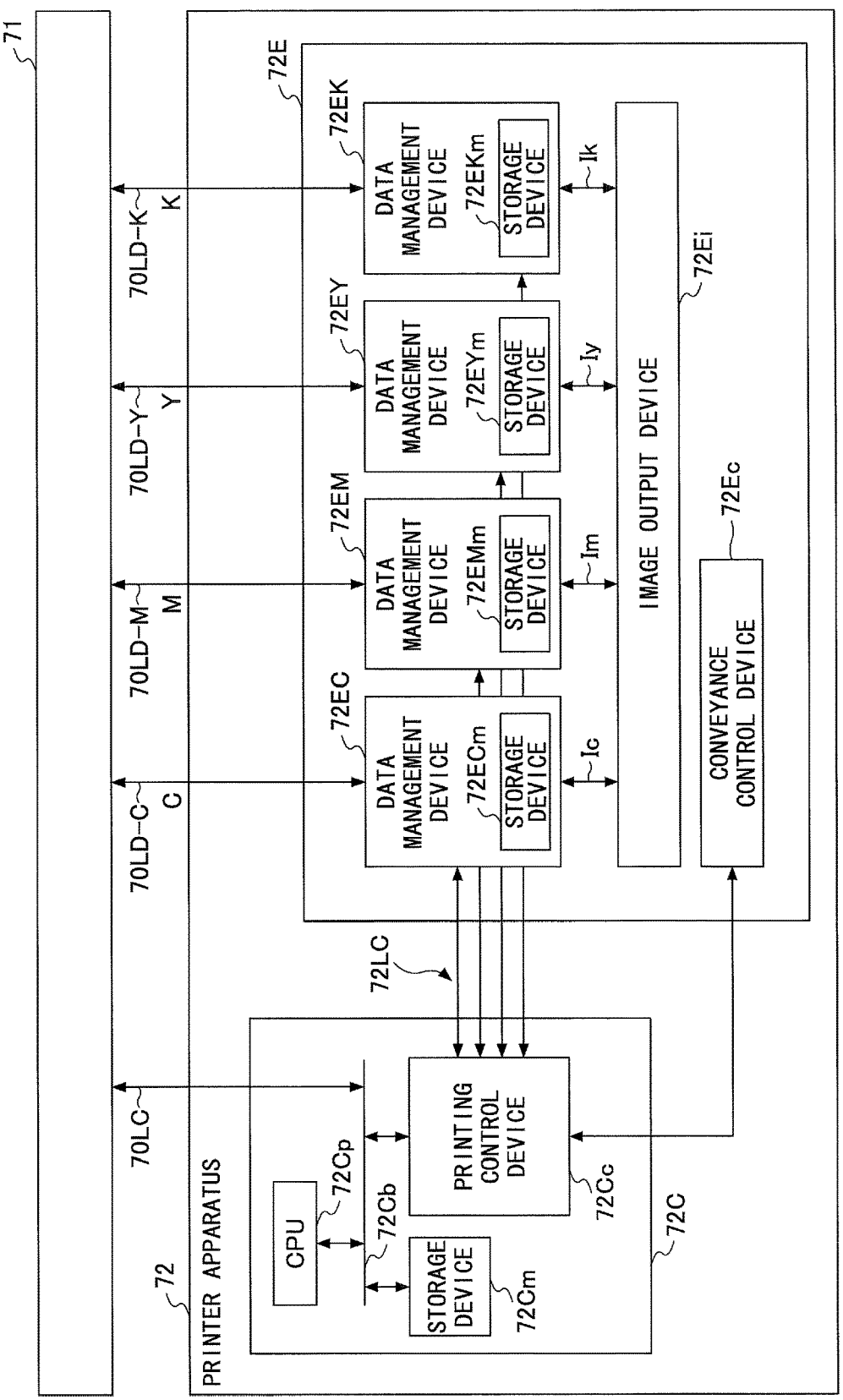
FIG. 12 is a block diagram illustrating one example of a hardware configuration of a control unit according to the embodiment of the present invention.

FIG. 12 is a block diagram illustrating one example of a hardware configuration of the controller 520 according to the embodiment of the present invention. For example, the controller 520 includes a host apparatus 71 such as an information processing apparatus, and a printer apparatus 72. In the illustrated example, the controller 520 causes the printer apparatus 72 to form an image on the recording medium based on image data, and control data that are input from the host apparatus 71.

The host apparatus 71 is, for example, a PC (Personal Computer), or the like. The printer apparatus 72 includes a printer controller 72C and a printer engine 72E.

The printer controller 72C controls operation of the printer engine 72E. First, the printer controller 72C transmits control data to and receives control data from the host apparatus 71 via a control line 70LC. Also, the printer controller 72C transmits control data to and receives control data from the printer engine 72E via a control line 72LC. As a result, various printing requirements and so forth indicated by the control data are input to the printer controller 72C, and the printer controller 72C stores the printing requirements and so forth in registers, or the like. Next, the printer controller 72C controls, based on the control data, the printer engine 72E to form an image according to printing job data, that is, the control data.

The printer controller 72C includes a CPU 72Cp, a printing control unit 72Cc, and a storage unit 72Cm. Note that the CPU 72Cp and the printing control unit 72Cc are connected via a bus 72Cb, and carry out communications therebetween. Also, the bus 72Cb is connected to the control line 70LC through a communications interface (I/F).

The CPU 72Cp controls the entirety of the printer apparatus 72 according to a control program, or the like. That is, the CPU 72Cp acts as a computing device and a control device.

The printing control unit 72Cc transmits commands or data indicating statuses or the like to and receives commands or data indicating statuses or the like from the printer engine 72E according to the control data transmitted by the host apparatus 71. Thus, the printing control unit 72Cc controls the printer engine 72E.

To the printer engine 72E, data lines 70LD-C, 70LD-M, 70LD-Y, and 70LD-K, i.e., a plurality of data lines, are connected. The printer engine 72E receives image data from the host apparatus 71 via the data lines. The printer engine 72E forms a color image under the control of the printer controller 72C.

The printer engine 72E includes data management devices 72EC, 72EM, 72EY, and 72EK, i.e., a plurality of data management devices. Also, the printer engine 72E includes the image output device 72Ei and a conveyance control unit 72Ec.

Figure 13:
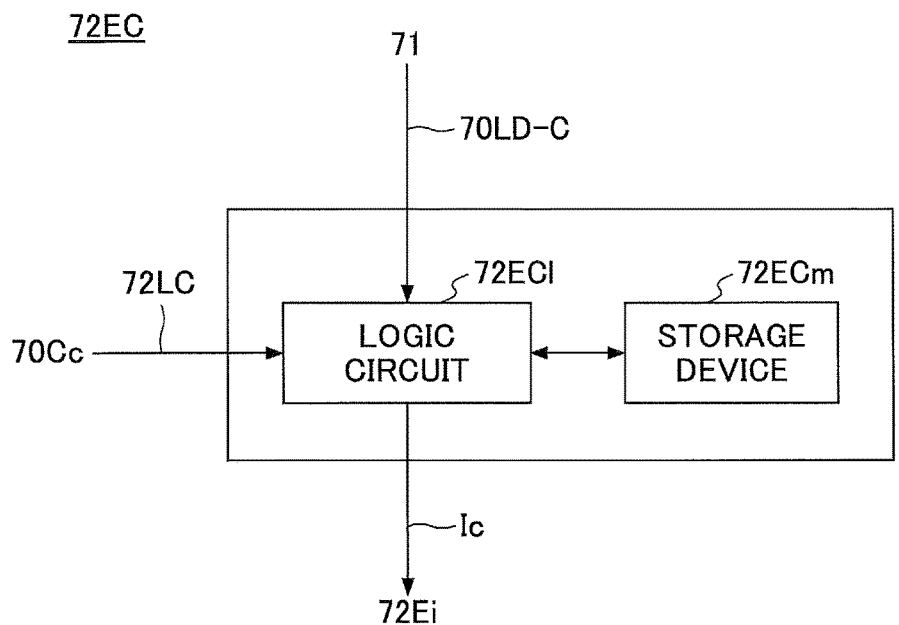
FIG. 13 is a block diagram illustrating one example of a hardware configuration of a data management device of the control unit according to the embodiment of the present invention.

FIG. 13 is a block diagram illustrating one example of a hardware configuration of each data management device of the control unit according to the embodiment of the present invention. For example, the data management devices 72EC, 72EM, 72EY, and 72EK have the same hardware configurations, for example. Hereinafter, assuming that the data management devices have the same hardware configurations, the data management devices 72EC will be described, as one example. Duplicate description will be omitted.

The data management device 72EC includes a logic circuit 72EC1 and a storage unit 72ECm. As illustrated, the logic circuit 72EC1 is connected to the host apparatus 71 via the data line 70LD-C. Also, the logic circuit 72EC1 is connected to the printing control unit 72Cc via the control line 72LC. Note that, the logic circuit 72EC1 is implemented by an ASIC (Application Specific Integrated Circuit), a PLD (Programmable Logic Device), or the like.

The logic circuit 72EC1 stores image data that is input from the host apparatus 71 in the storage unit 72ECm based on the control signal that is input from the printer controller 72C (see FIG. 12).

Also, the logic circuit 72EC1 reads, from the storage unit 72ECm, image data Ic for cyan based on the control signal that is input from the printer controller 72C. Next, the logic circuit 72EC1 sends the thus read image data Ic for cyan to the image output device 72Ei.

It is desirable that the storage unit 72ECm has a storage capacity to store three pages of image data, for example. If three pages of image data can be stored, the storage unit 72ECm can store image data that is input from the host apparatus 71, image data that is used to form an image, and image data for forming a next image.

Figure 14:
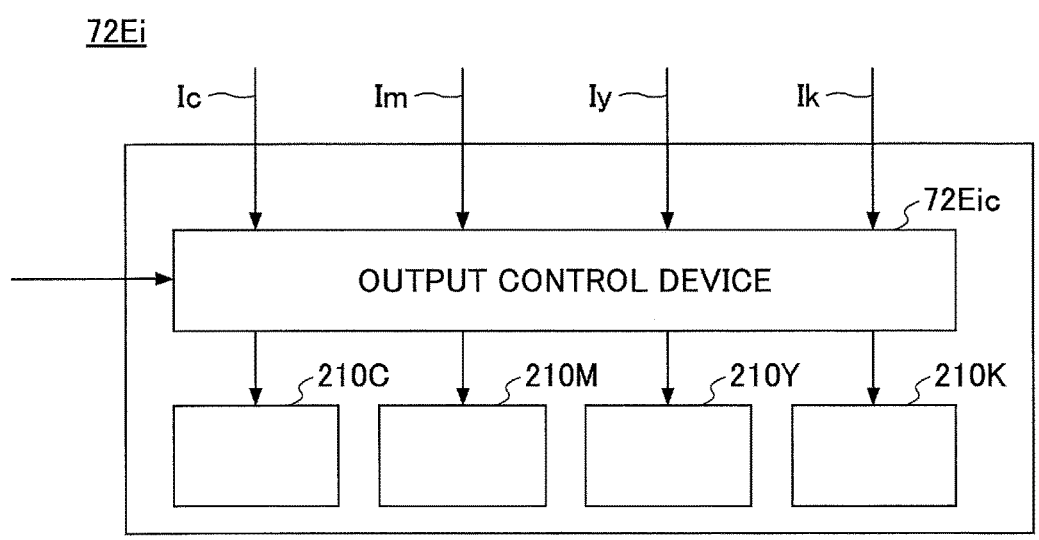
FIG. 14 is a block diagram illustrating one example of a hardware configuration of the control unit according to the embodiment of the present invention.

FIG. 14 is a block diagram illustrating one example of a hardware configuration of the image output device 72Ei according to the embodiment of the present invention. As illustrated, the image output device 72Ei includes an the output control unit 72Eic, the black liquid firing head unit 210K, the cyan liquid firing head unit 210C, the magenta liquid firing head unit 210M, and the yellow liquid firing head unit 210Y, i.e., the liquid firing head units of the respective colors.

The output control unit 72Eic outputs image data of each color to the corresponding liquid firing head unit. That is, the output control unit 72Eic controls the respective liquid firing head units 210K-210Y according to the image data of the respective colors.

The output control unit 72Eic controls the liquid firing head units 210K-210Y simultaneously or separately. That is, the output control unit 72Eic receives information of the timings to control the liquid firing head units 210K-210Y to fire liquid droplets in such a manner as to change the liquid droplet firing timings, for example. Note that, the output control unit 72Eic may control any of the liquid firing head units 210K-210Y based on a control signal that is input from the printer controller 72C (see FIG. 12). Also, the output control unit 72Eic may control any of the liquid firing head units 210K-210Y based on an operation performed by the user, or the like.

In the example of the printer apparatus 72 illustrated in FIG. 12, the signal path of inputting image data from the host apparatus 71 and the signal path of signal transmission and reception between the host apparatus 71 and the printer apparatus 72 based on the control data are different paths.

The printer apparatus 72 may have a configuration such as to form an image with a single black color. In this case, in order to increase the speed of forming an image, it is possible that, for example, the printer apparatus 72 includes the single data management device and the four black liquid firing head units. Thereby, the black liquid firing head units fire black ink droplets, respectively. Therefore, in comparison to a case of using the single black liquid firing head unit, it is possible to carry out image formation at higher speed.

The conveyance control unit 72Ec (FIG. 12) is an actuator mechanism, a driver device, and so forth, for conveying the web 120. For example, the conveyance control unit 72Ec controls a motor connected to each roller, or the like, to cause the roller or the like to convey the web 120.

Example of Overall Processing

Figure 15:
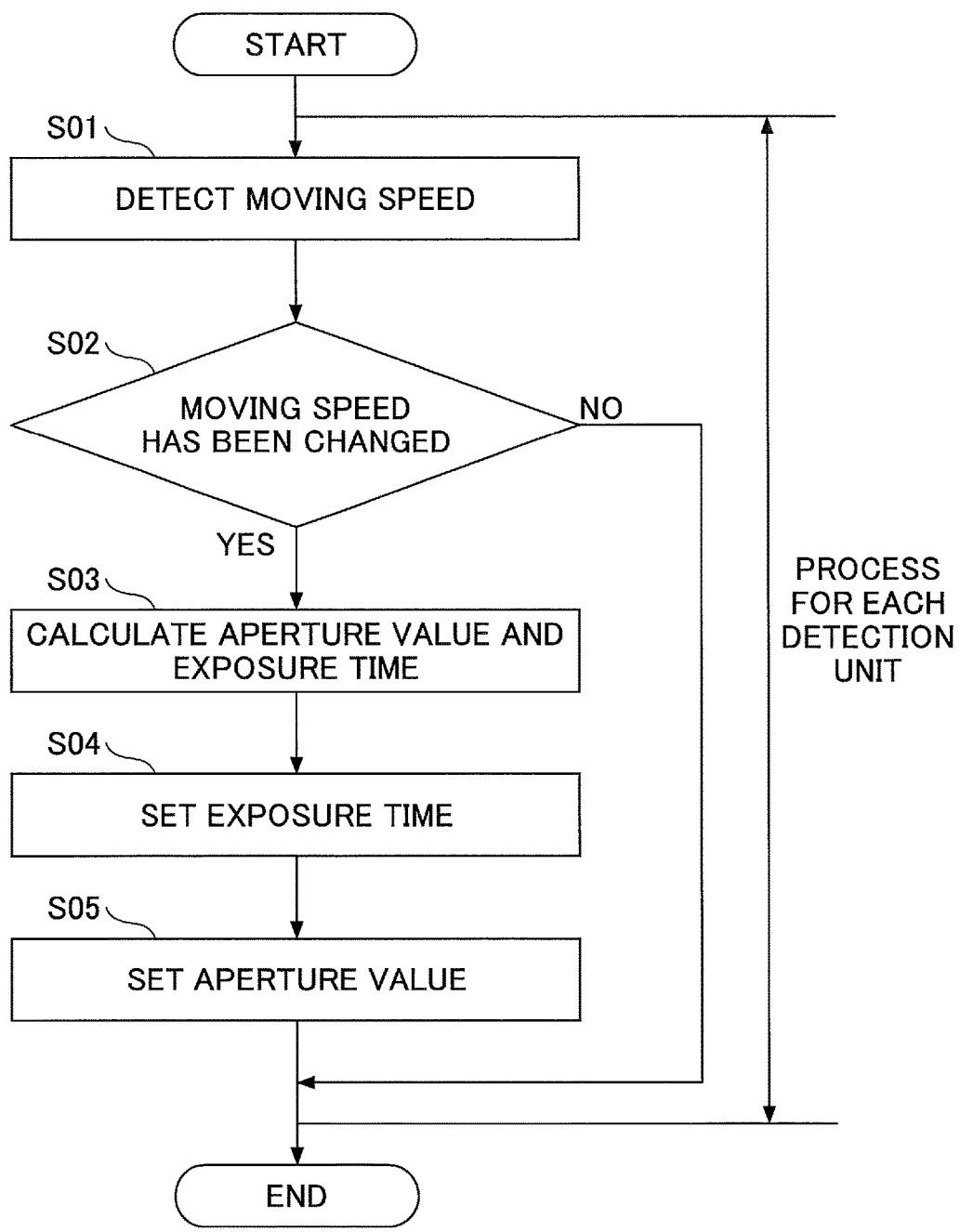
FIG. 15 is a flowchart illustrating one example of overall processing of an apparatus that fires liquid droplets according to the embodiment of the present invention.

FIG. 15 is a flowchart illustrating one example of overall processing of the apparatus that fires liquid droplets according to the embodiment of the present invention. The overall processing illustrated in FIG. 15 is one example of a conveyed object detection method carried out by a conveyed object detection apparatus included in the image forming apparatus 110.

For example, previously, image data indicating an image to be formed on the web 120 (see FIG. 1) is input to the image forming apparatus 110. Next, the image forming apparatus 110 carries out the overall processing illustrated in FIG. 15 based on the image data, to form the corresponding image on the web 120.

In step S01, the image forming apparatus 110 detects the moving speed of the web 120 in the conveyance direction or the lateral direction. That is, in step S01, the image forming apparatus uses the sensor to detect the moving speed at which the web 120 is conveyed in at least one of the conveyance direction or the lateral direction.

In step S02, the image forming apparatus determines, based on the moving speed detected in step S01, whether the moving speed has been changed. Next, if the image forming apparatus determines that the moving speed has been changed (YES in step S02), the image forming apparatus proceeds to step S03. On the other hand, if the image forming apparatus determines that the moving speed has not been changed (NO in step S02), the image forming apparatus ends the process.

In step S03, the image forming apparatus calculates the aperture value and the exposure time. For example, the aperture value and the exposure time are calculated by the following Formulas (4).

$$I = Io \times (NA \times Mo)^2$$

$$\text{(depth of focus)} = \pm k \times \text{(wavelength)} / \{2 \times \text{(numerical aperture)}^2\} \quad (4)$$

Formulas (4) will be described later

In step S04, the image forming apparatus sets the shutter speed and so forth such that the exposure time calculated in step S03 will be acquired.

In step S05, the image forming apparatus sets the aperture value calculated in step S03.

Figure 16:
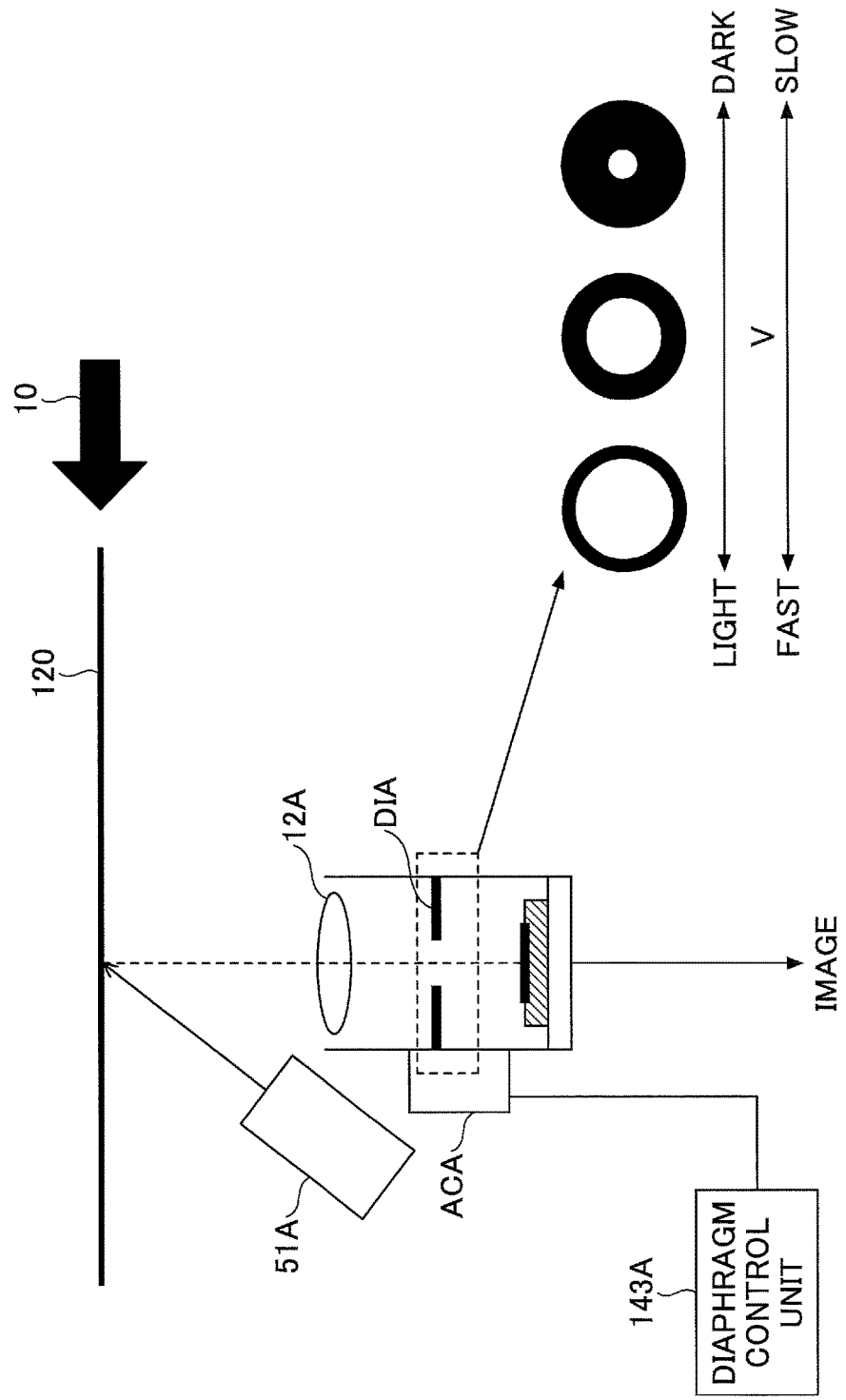
FIG. 16 illustrates one example of a diaphragm that the apparatus that fires liquid droplets according to the embodiment of the present invention has.

FIG. 16 illustrates one example of the diaphragm that the apparatus that fires liquid droplets according to the embodiment of the present invention has. After the process illustrated in FIG. 15 is carried out, the diaphragm is controlled, for example, as illustrated in FIG. 16.

Below, it is assumed that the electrical iris diaphragm such as that illustrated in FIG. 16 is used, for example. As illustrated, the diaphragm DIA has the aperture area changed based on the aperture value that is set. If the moving speed of the web 120 is increased, a blur may occur in the taken image. In particular, concerning the conveyance direction, a blur may likely to occur. In order to reduce an influence of such a blur, the shutter speed is increased, i.e., the exposure time is reduced.

As the exposure time is thus reduced, the exposure amount may likely to be reduced. Thus, as the exposure time is reduced, the taken image may likely to become darker. If the image becomes darker, the calculation precision concerning the image correlation may likely to degrade. Therefore, the detection precision concerning the position, the moving speed, the moved amount, or the like, detected by the detection unit, may likely to degrade.

Therefore, when the moving speed V will be thus increased, the image forming apparatus increases the aperture area to receive a much amount of light. Thus, the image forming apparatus can take a light image. Using such a light image, the image forming apparatus can improve the signal-to-noise ratio of the image, to improve the precision of detecting the position, or the like, of the web 120.

In order to take a light image, there may be another method of increasing the illumination light intensity. However, it is desirable to reduce the illumination light intensity from the energy saving viewpoint or the safety improving viewpoint. In order to improve the precision of detecting the position, or the like, of the web 120, it is desirable to increase the number of pixels used for the calculation or the optical magnification to increase the resolution for each pixel. By thus setting the aperture value, and so forth, according to the embodiment of the present invention, it is possible to reduce the illumination light intensity.

Note that, the aperture value may be set continuously or discretely.

If the light source has variations in its light emittance intensity or the CMOS sensor has variations in its sensitivity, the image forming apparatus may adjust the light reception amount based on the variations.

In step S03 illustrated in FIG. 15, the aperture value is calculated such that the light reception amount in inverse proportion to the exposure time determined by the moving speed V will be acquired. For example, the aperture value is calculated by the above-mentioned Formulas (4).

In Formulas (4), "I" represents the lightness of an image, and "Io" represents the lightness on the specimen surface. In Formulas (4), "NA" represents the numerical aperture that is one example of the aperture value. Also, in Formulas (4), "Mo" represents the magnification of an objective lens. That is, the numerical aperture is set in the diaphragm. In case of Formulas (4), the light reception amount is in proportion to the second power of the numerical aperture, and therefore, in order to halve the exposure time, the numerical aperture is increased $\sqrt{2}$ times.

Note that, it is possible that, through experiments or evaluations carried out previously, the image forming apparatus may previously store the exposure time and the aperture value with respect to the moving speed in a form of a lookup table, or the like. In this case, the setting unit 55F determines the exposure time and the aperture value corresponding to the moving speed from the lookup table, or the like, to set the exposure time and the aperture value, for example.

Figure 17:
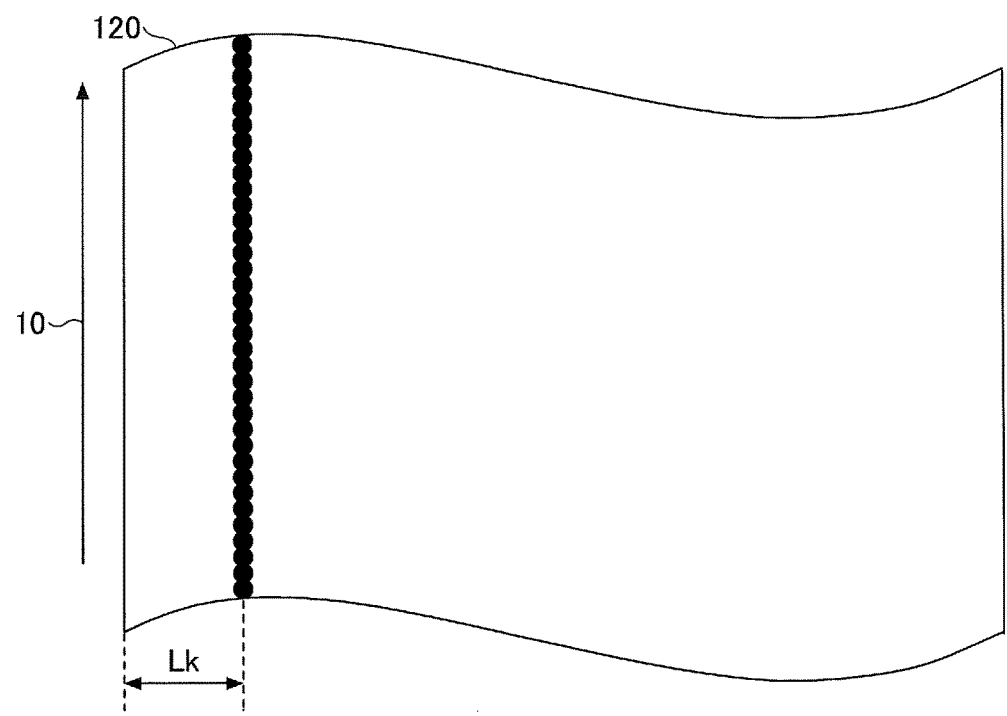
FIG. 17 illustrates one example of a test pattern used by the apparatus that fires liquid droplets according to the embodiment of the present invention.

FIG. 17 illustrates one example of a test pattern used by the apparatus that fires liquid droplets according to the embodiment of the present invention. First, as illustrated, the image forming apparatus carries out test printing with black that is one example of the first color to form a straight line in the conveyance direction 10. From the result of the test printing, the distance Lk from an edge is acquired. Then, concerning the lateral direction, the distance Lk from the edge is adjusted manually or automatically through the apparatus. Thus, the position at which an ink of the first color, that is, black, that is a reference color, is determined. Note that, the actual method to determine the position of firing the black ink is not limited to this method.

Figure 18A:
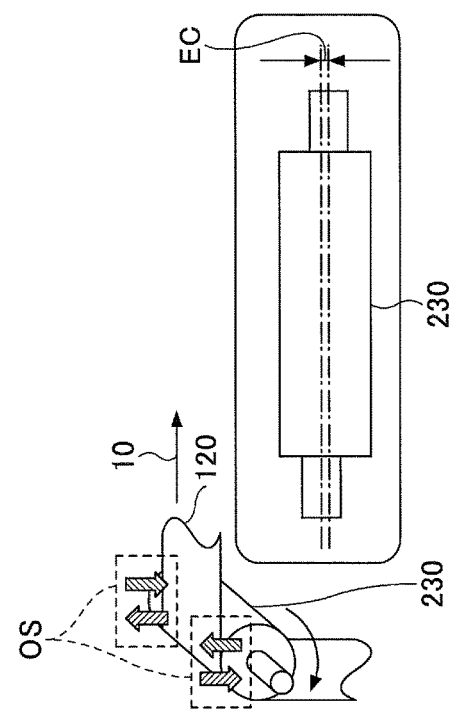
FIGS. 18A-18C illustrates one example of a result of a process of the apparatus that fires liquid droplets according to the embodiment of the present invention.
Figure 18C:
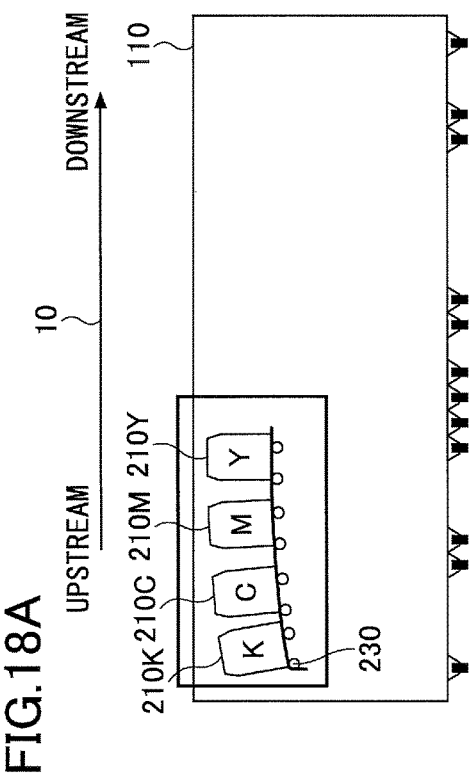
Figure 18B:
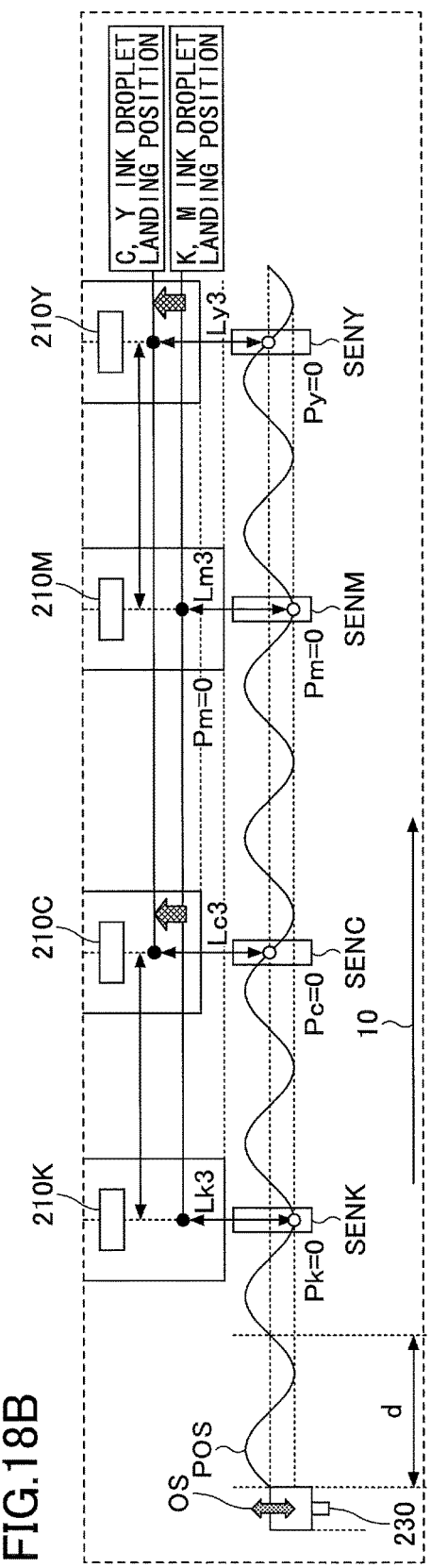

FIGS. 18A-18C illustrates one example of a result of a process of the apparatus that fires liquid droplets according to the embodiment of the present invention. For example, as illustrated in FIG. 18B, it is assumed that images of black, cyan, magenta, and yellow are formed in the stated order. FIG. 18B illustrates a so-called plan view viewed from the top of FIG. 18A. Below, it is assumed that the roller 230 has an eccentricity, for example. Actually, as illustrated in FIG. 18C, it is assumed that an eccentricity EC is present, for the purpose of explanation. Due to the eccentricity EC, while the web 120 is conveyed, the roller 230 has an oscillation OS. Due to the oscillation OS, the position POS of the web 120 varies accordingly. That is, the oscillation OS causes "meandering".

In order to reduce a color shift with respect to black, the following operations will be carried out, for example. Note that the image forming apparatus subtracts, from the currently detected position of the recording medium, the position of the recording medium detected one cycle before, to calculate the positional variation of the recording medium (the web 120). In this regard, "Pk" denotes the difference between the position of the web 120 detected by the sensor SENK for black and the position of the web 120 below the black liquid firing head unit 210K is "Pk". Here, it is assumed that "Pk=0" holds. On the other hand, "Pc" denotes the difference between the position of the web 120 detected by the sensor SENC for cyan and the position of the web 120 detected by the sensor SENK for black. It the same way, "Pm" denotes the difference between the position of the web 120 detected by the sensor SENM for magenta and the position of the web 120 detected by the sensor SENK for black. Also, "Py" denotes the difference between the position of the web 120 detected by the sensor SENY for yellow and the position of the web 120 detected by the sensor SENK for black.

"Lk3", "Lc3", "Lm3", and "Ly3" denote the distances of the positions at which liquid droplets will land from the respective liquid firing head units from the web 120 edge, that is, the distances from an edge of the web 120, for the respective colors. The sensors detect the positions of the web 120, respectively.

If there are no positional variations of the web 120 in the lateral direction, the equations, "Pk=0", "Pc=0", "Pm=0", and "Py=0", hold. However, for example, it is assumed that "Pc" and "Py" are both not zero whereas "Pk" and "Py" are both zero, as illustrated in FIG. 18B, due to positional variations of the web 120 in the lateral direction occurring due to some cause. According to the embodiment of the present invention, such variations will be canceled out, as illustrated in the following Formulas (5), for example.

$$Lc3=Lk3-Pc=Lk3$$

$$Lm3=Lk3$$

$$Ly3=Lk3-Py=Lk3 \quad (5)$$

Thus, the equation "Lk3=Lm3=Lc3=Ly3" will be acquired, by moving the cyan liquid firing head unit 210C and the yellow liquid firing head unit 210Y by the amounts of Pc and Py, respectively. Thus, as a result of the image forming apparatus controlling the positions of the respective liquid firing head units 120K-120Y to cancel out the positional variations of the web 120, the image forming apparatus can improve the precision of the fired liquid landing positions. Because the liquid of each color thus lands on the web 120 with high accuracy, it is possible to reduce color shifts, to improve the image quality of the thus formed image.

Also, it is desirable that the position at which the corresponding sensor is installed is nearer to the first roller than the landing position.

FIG. 19 illustrates one example of the position at which the sensor is installed in the apparatus that fires liquid droplets according to the embodiment of the present invention. Now, description will be made for black, as one example. In this example, It is desirable that the sensor SENK for black is installed nearer to the first roller CR1K for black than the black landing position PK, between the first roller CR1K for black and the second roller CR2K for black. Note that, the distance at which the sensor SENK for black is thus made to approach the first roller CR1K for black depends on the time used for the control operation, or the like. For example, the distance at which the sensor SENK for black is made to approach the first roller CR1K for black is determined as "20 mm". This case is an example where the sensor SENK for black is installed at the "20 mm" upstream side from the black landing position PK.

As a result of the position at which the sensor is installed being thus made to be close to the landing position, the detection error E1 is reduced. As a result of the detection error E1 being reduced, the image forming apparatus can land liquid droplets for each color with high accuracy. Therefore, upon forming an image, the image forming apparatus can land liquid droplets for each color with high accuracy, and thus, it is possible to reduce a color shift to improve the image quality of the image.

As a result of using the above-mentioned configuration, there is no restriction to make the distance between the liquid firing head units to be an integral multiple of the circumferential length d of the roller (see FIG. 18). Therefore, it is possible to freely determine the position at which each liquid firing head unit is installed. In other words, in the image forming apparatus, it is possible to land liquid droplets for each color with high accuracy even if the distance between the respective liquid firing head units is not equal to an integral multiple of the circumferential length d of the roller.

Comparison Examples

FIG. 20 illustrates a hardware configuration of a first comparison example. The illustrated first comparison example detects the position of the web 120 before each liquid firing head unit reaches the position to fire a liquid droplet. For example, in the comparison example, the sensor is installed at the distance "200 mm" from the position immediately below the liquid firing head unit. Based on the detection result, the image forming apparatus of the first comparison example cancels out the positional variations of the recording medium by moving the liquid firing head units.

Figure 21:
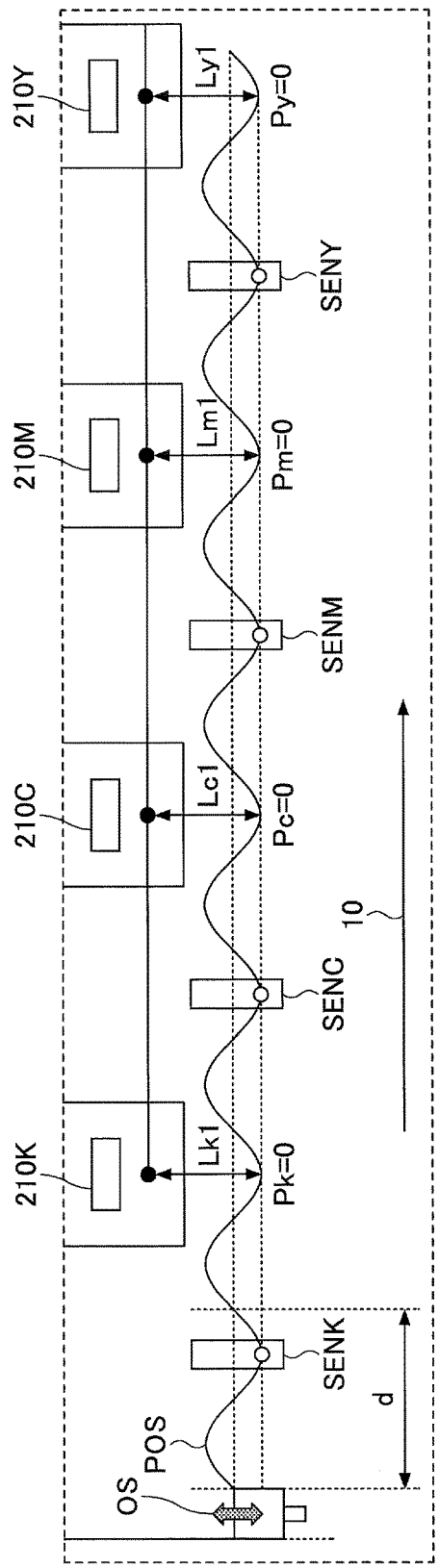
FIG. 21 illustrates a process result example of an apparatus that fires liquid droplets in the first comparison example.

FIG. 21 illustrates a process result example of an apparatus that fires liquid droplets in the first comparison example. In this comparison example, the liquid firing head units are installed in such a manner that the distance between the respective liquid firing head units will be an integral multiple of the circumferential length d of the roller. In this case, the difference between the web's position detected by each sensor and the web's position immediately bellow the liquid firing head unit is "0". Therefore, in the comparison example, the relationships "Lk1=Lc1=Lm1=Ly1" holds where "Lk1", "Lc1", "Lm1", and "Ly1" denote respective distances of landing positions of ink droplets of the respective colors from the edge of the web. Thus, image quality degradation due to the positional shifts of the web 120 is avoided thanks to the settings of the distance between the respective liquid firing head units to be an integral multiple of the circumferential length d of the roller.

Figure 22:
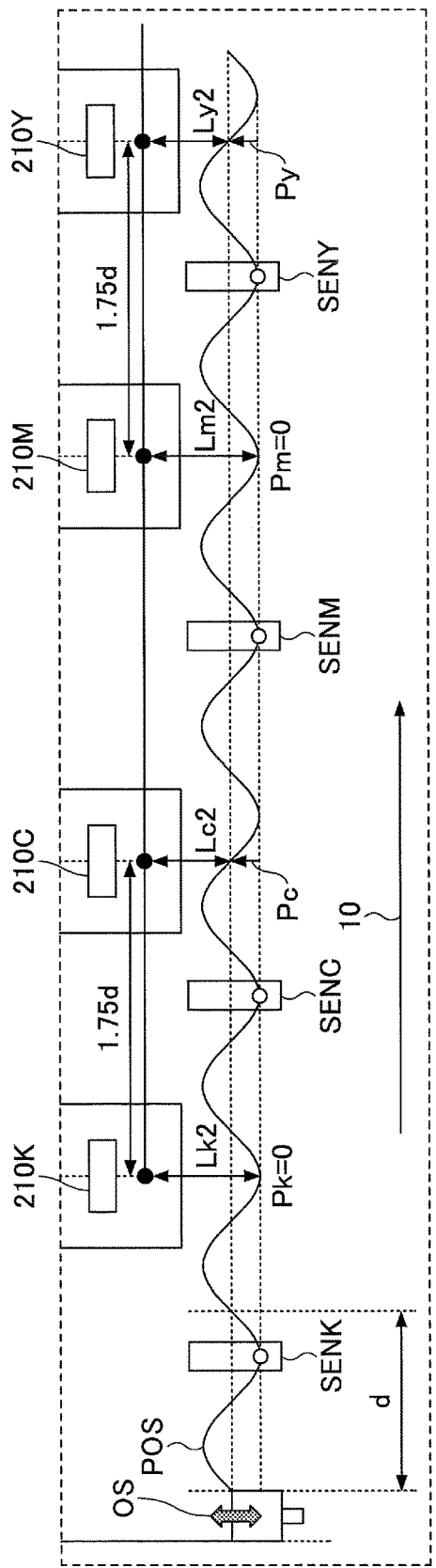
FIG. 22 illustrates a process result example of an overall process of an apparatus that fires liquid droplets in a second comparison example.

FIG. 22 illustrates a process result example of an overall process of an apparatus that fires liquid droplets in a second comparison example. Note that, the second comparison example have the same hardware configuration as the first comparison example. In comparison to the first comparison example, the second comparison example is different in that each of the distance between the black and cyan liquid firing head units and the distance between the magenta and yellow liquid firing head units is "1.75d". That is, the second comparison example is such that each of the distance between the black and cyan liquid firing head units and the distance between the magenta and yellow liquid firing head units is not an integral multiple of the circumferential length d of the roller.

In the second comparison example, "Pk" denotes the difference between the web's position detected by the sensor SENK for black and the web's position below the black liquid firing head unit 210K. In the same way, "Pc" denotes the difference between the web's position detected by the sensor SENC for cyan and the web's position below the cyan liquid firing head unit 210C. In the same way, "Pm" denotes the difference between the web's position detected by the sensor SENM for magenta and the web's position below the magenta liquid firing head unit 210M. In the same way, "Py" denotes the difference between the web's position detected by the sensor SENY for yellow and the web's position below the yellow liquid firing head unit 210C. Also, "Lk2", "Lc2", "Lm2", and "Ly2" denote the distances of the landing positions of ink droplets of the respective colors from the edge of the web. In this case, the relationships of the following Formulas (6) hold:

$$Lc2=Lk2-Pc$$

$$Lm2=Lk2$$

$$Ly2=Lk2-Py \quad (6)$$

Thus the relationships "Lk2=Lm2≠Lc2=Ly2" are acquired. Thus, as a result of the distances between the respective liquid firing head units being not an integral multiple of the circumferential length d of the roller, as in this comparison example, the web's positions immediately below the cyan liquid firing head unit 210C and the magenta liquid firing head unit 210M are shifted by the amounts "Pc" and "Py", respectively, and therefore, are different. Therefore, image quality degradation due to positional variations of the web 210 may occur, and thus, a color shift or the like may likely to occur.

Figure 23:
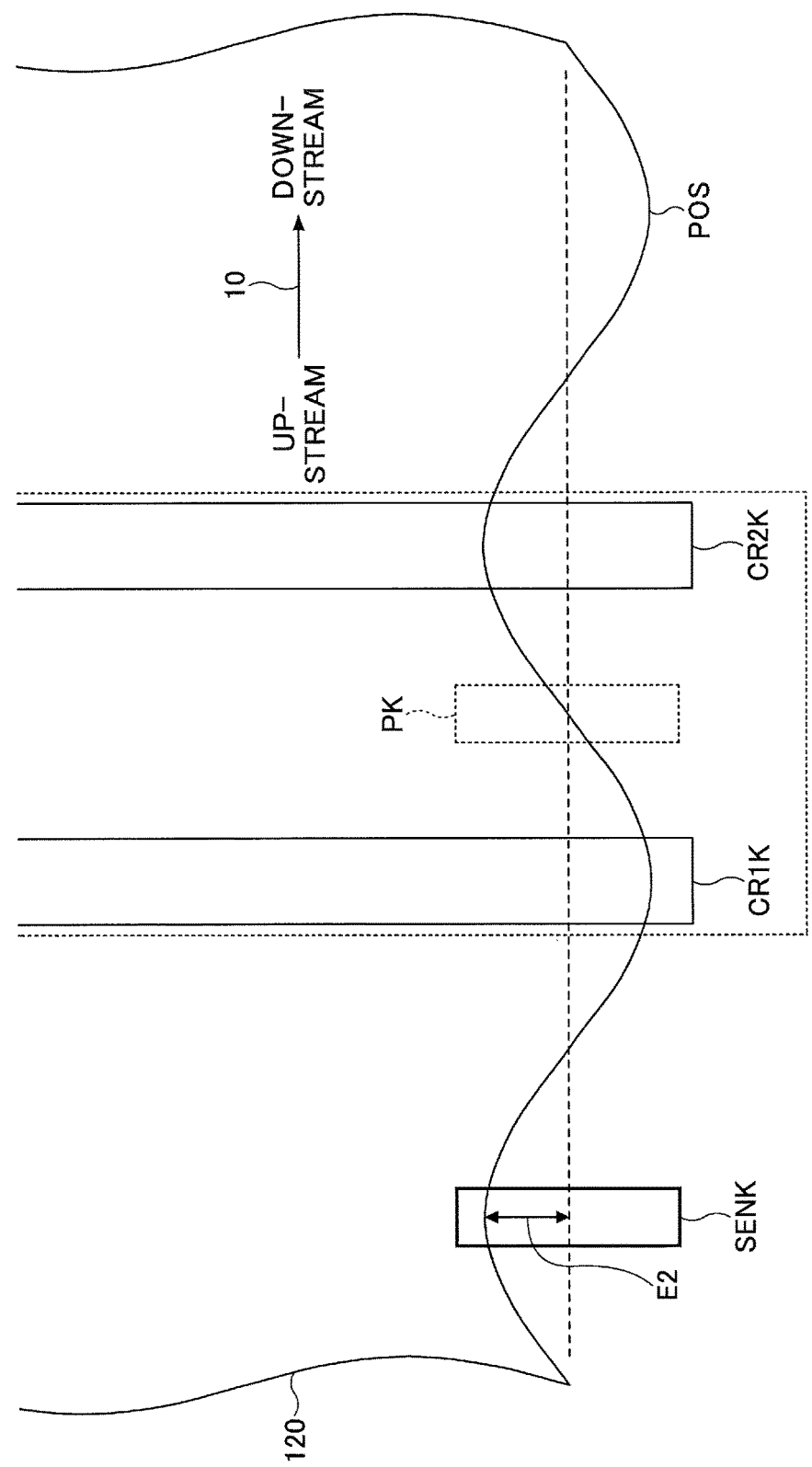
FIG. 23 illustrates one example of a position of a sensor in an apparatus that fires liquid droplets in a third comparison example.

FIG. 23 illustrates one example of the position of the sensor in an apparatus that fires liquid droplets in a third comparison example. As illustrated, in this comparison example, the sensor is installed farther than the landing position. Therefore, in many cases, the detection error E2 in the comparison example may be increased.

Functional Configuration Example

Figure 24:
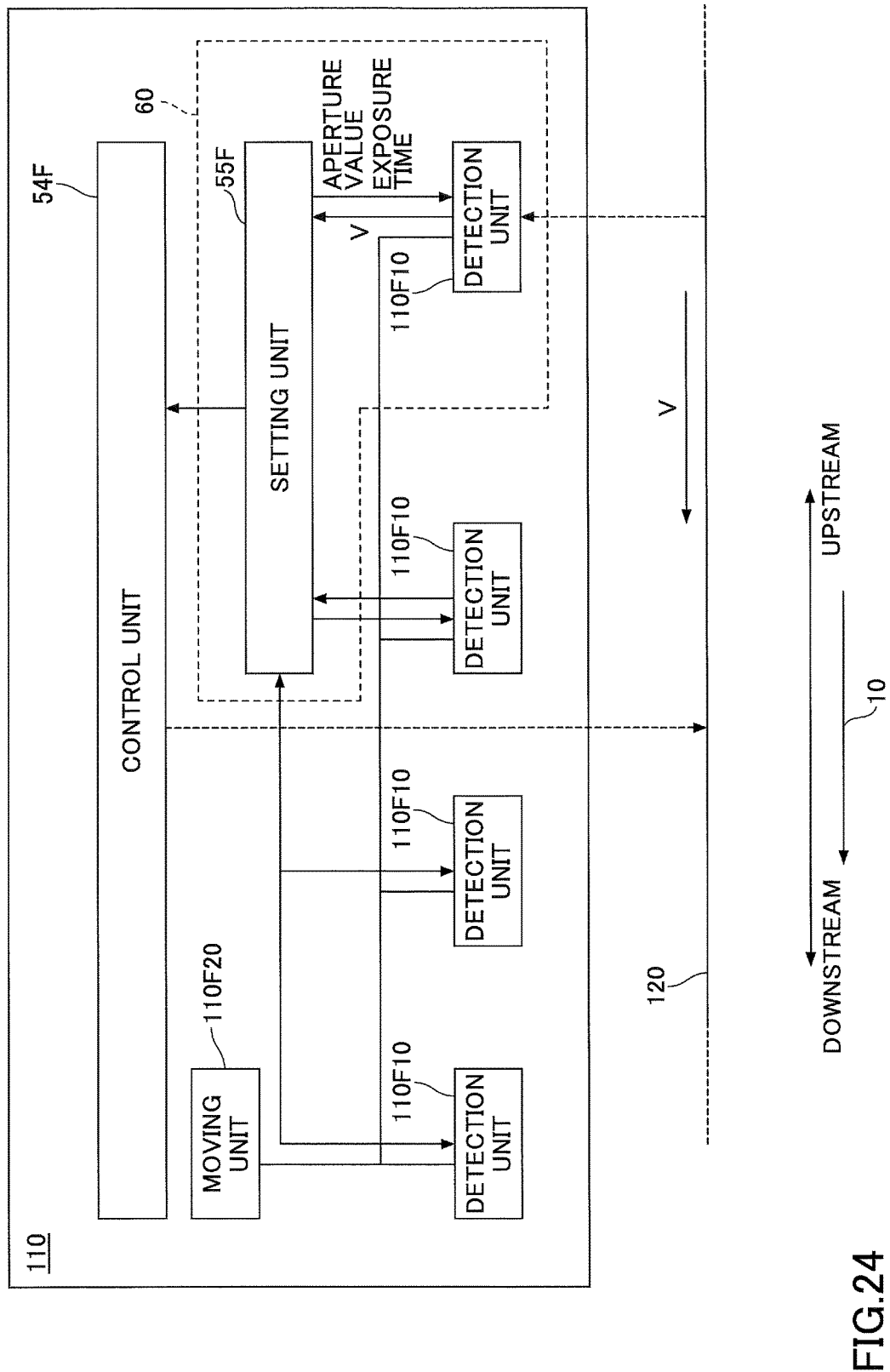
FIG. 24 is a functional block diagram illustrating one example of a functional configuration of the apparatus that fires liquid droplets according to the embodiment of the present invention.

FIG. 24 is a functional block diagram illustrating one example of a function configuration of the apparatus that fires liquid droplets according to the embodiment of the present invention. As illustrated, the image forming apparatus 110 includes the plurality of liquid firing head units, and the detection unit 110F10 for each of the liquid firing head units. Also, the image forming apparatus 110 includes, as illustrated, the control unit 54F. Then, the conveyed object detection apparatus 60 included in the image forming apparatus 110 includes a detection unit 110F10 and the setting unit 55F.

The detection unit 110F10 is provided for, as illustrated, each of the liquid firing head units. Actually, as the illustrated in FIG. 2, the number of detection units 110F10 is 4, as illustrated. Each detection unit 110F10 detects the position or the moved amount of the recording medium (i.e., the web 120) in the conveyance direction or the lateral direction. Note that, each detection unit 110F10 has a hardware configuration, for example, illustrated in FIG. 4, FIG. 9, or the like. The detection unit 110F10 uses the optical sensor to output the detection result of the moving speed of the conveyed object in at least one of the conveyance direction in which the conveyed object is conveyed or the lateral direction. Note that, each detection unit 110F10 includes the detection units 52A and 52B, and so forth, illustrated in FIG. 9.

The first supporting member is installed, as illustrated in FIG. 2, for each of the liquid firing head units. Actually, in the example of FIG. 2, the number of the first supporting members is the same as the number of the liquid firing head units, and is 4. The first supporting member is the roller or the like used to convey the recording medium to such a position that the liquid firing head unit can fire liquid droplets at the landing position that is a predetermined position of the recording medium. That is, the first supporting member is the first roller installed on the upstream side of each landing position, or the like. Note that the first roller is the first roller CR1K for black (see FIG. 2), for example.

The second supporting member is installed, as illustrated in FIG. 2, for each of the liquid firing head units. Actually, in the example of FIG. 2, the number of the second supporting members is the same as the number of the liquid firing head units, and is 4. The second supporting member is the roller or the like used to convey the recording medium from the landing position to another position. That is, the second supporting member is the second roller installed on the downstream side of each landing position. Note that the second roller is the second roller CR2K for black (see FIG. 2), for example.

The setting unit 55F sets the aperture value and the exposure time concerning the optical sensor that the detection unit 110F10 uses, based on the moving speed.

Note that, it is desirable that, as illustrated, the image forming apparatus 110 further includes a moving unit 110F20 (see FIG. 24) moving the respective liquid firing head units based on the detection results. For example, the moving unit 110F20 has the following hardware configuration.

Figure 25:
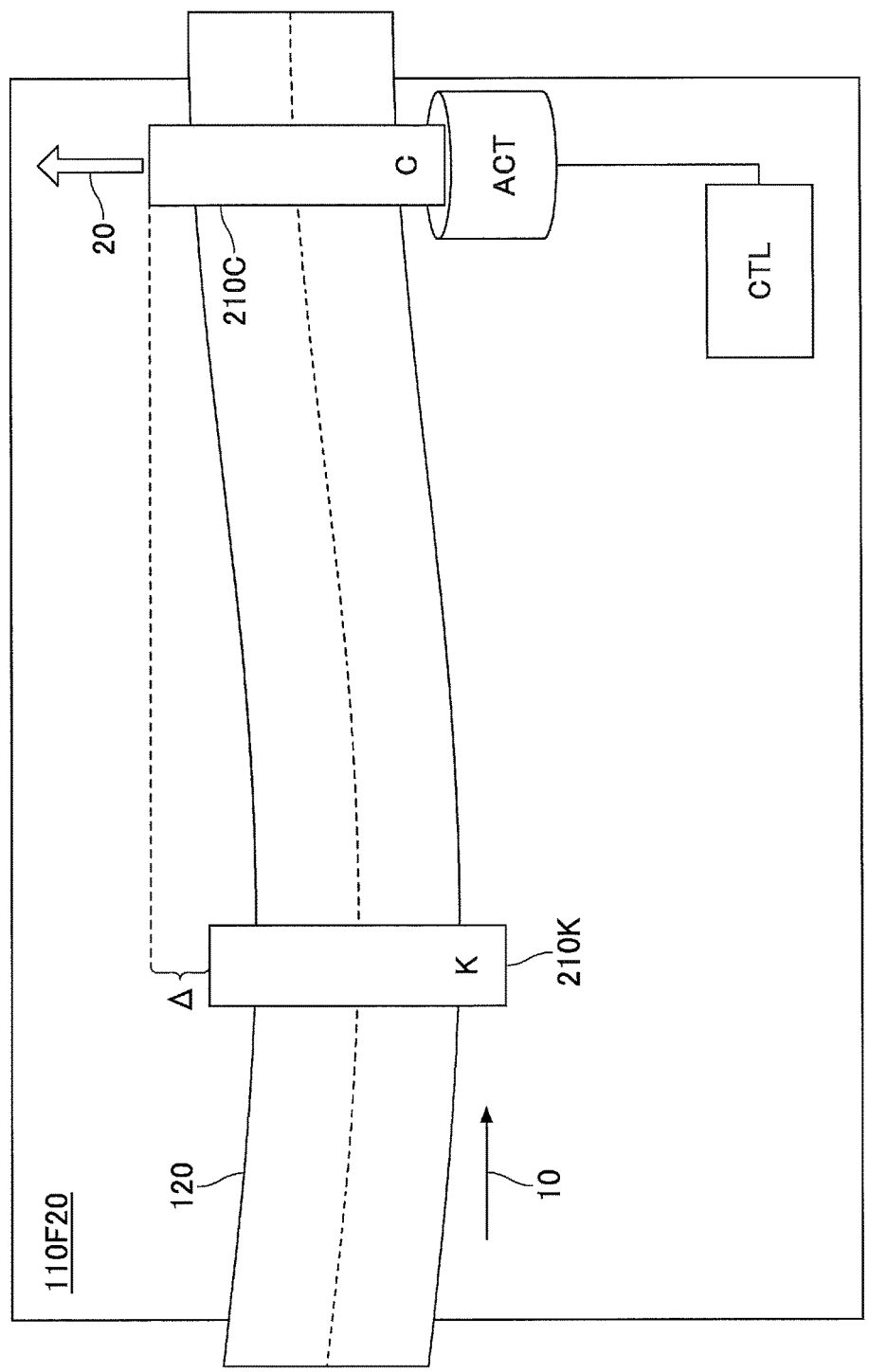
FIG. 25 is a block diagram illustrating one example of a hardware configuration for moving a liquid firing head unit that the apparatus that fires liquid droplets according to the embodiment of the present invention has.

FIG. 25 is a block diagram illustrating one example of a hardware configuration for moving the liquid firing head units that the apparatus that fires liquid droplets according to the embodiment of the present invention has. Below, as illustrated, a hardware configuration for moving the cyan liquid firing head unit 210C will be described, as one example.

First, in the illustrated example, the actuator ACT such as a linear actuator for moving the cyan liquid firing head unit 210C is installed for the cyan liquid firing head unit 210C. Then, to the actuator ACT, an actuator controller CTL controlling the actuator ACT is connected.

The actuator ACT is, for example, a linear actuator or a motor. The actuator ACT may also include a control circuit, a power supply circuit, mechanism components, and so forth.

The actuator controller CTL is, for example, a driver circuit, or the like. Then, the actuator controller CTL controls the position of the cyan liquid firing head unit 210C.

To the actuator controller CTL, the detection result of the corresponding detection unit 110F10 (see FIG. 24) is input. Then, the actuator controller CTL causes the actuator ACT to move the cyan liquid firing head unit 210C in such a manner as to cancel out the positional variations of the web 120 indicated by the detection result.

In the illustrated example, the detection result indicates, for example, a positional variation Δ. Therefore, in this example, the actuator controller CTL moves the cyan liquid firing head unit 210C in the lateral direction 20 to cancel the positional variation Δ.

Note that, the hardware of the controller 520 illustrated in FIG. 2 and so forth and the hardware illustrated in FIG. 24 to move the liquid firing head unit may be included in one unit or may be respective separate units.

Returning FIG. 24, it is desirable that the position at which the corresponding detection unit 110F10 carries out the detection, that is, the position at which the sensor or the like is installed, is near the corresponding landing position such as the black landing position PK, as in the interval INTK1 between the rollers for black. That is, if the detection is carried out in the interval INTK1 between the rollers for black (FIG. 2), the image forming apparatus 110 can detect the position or the like of the recording medium in the conveyance direction or the lateral direction with high accuracy.

It is also desirable that the position at which the detection unit 110F10 carries out the detection, that is, the position at which the sensor or the like is installed, is on the upstream side of the landing position between the respective rollers, as in the upstream interval INTK2 for black (see FIG. 2). That is, if the detection is carried out in the upstream interval INTK2 for black, the image forming apparatus 110 can detect the position or the like of the recording medium in the conveyance direction or the lateral direction with high accuracy.

Thus, the image forming apparatus 110 can calculate, based on the detection result of the detection unit 110F10, the timing for each liquid firing head unit to fire liquid droplets; the moving amount to move each liquid firing head unit; or a combination of the timing and the moving amount.

That is, if the position is detected on the upstream side, and thereafter, the web 120 is conveyed to the landing position on the downstream side, calculation of the timing to fire liquid droplets, the amount of moving the liquid firing head unit, or a combination of the timing and the moving amount can be carried out during the conveyance. Therefore, each liquid firing head unit can control the landing position in the conveyance direction, the lateral direction, or both, with high accuracy.

Summary of Embodiments

The apparatus that fires liquid droplets according to the embodiment of the present invention includes the conveyed object detection apparatus having the optical sensor, or the like. The conveyed object detection apparatus 60 includes the detection unit 110F10 and the setting unit 55F, and sets, based on the moving speed, the aperture value and the exposure time. Thus, the conveyed object detection apparatus 60 can detect the position of the conveyed object in the conveyance direction or the lateral direction, or the like, with high accuracy.

In the apparatus that fires liquid droplets according to the embodiment of the present invention, for each liquid firing head unit, the position of the conveyed object such as the recording medium, in the conveyance direction or the lateral direction, is detected at a position near the liquid firing head unit. Next, based on the detection result, the apparatus that fires liquid droplets according to the embodiment of the present invention moves the liquid firing head unit. Therefore, according to the apparatus that fires liquid droplets according to the embodiment of the present invention, in comparison to the first comparison example, the second comparison example, and so forth, it is possible to correct a possible shift in the landing position of the liquid droplets in the conveyance direction or the lateral direction perpendicular to the conveyance direction with high accuracy.

Also, according to the apparatus that fires liquid droplets according to the embodiment of the present invention, different from the first comparison example, the respective liquid firing head units are not necessarily placed to have the intervals equal to an integral multiple of the circumferential length of the roller. Therefore, it is possible to reduce the restriction to install the respective liquid firing head units. Also, in the first comparison example and the second comparison example, adjustment is not possible for the first color, that is, in this example, black, because the examples do not have actuators to move the liquid firing head units. In contrast, according to the apparatus that fires liquid droplets according to the embodiment of the present invention, even concerning the first color, it is possible to improve the preciseness of the landing position of the fired liquid droplets in the conveyance direction or the lateral direction perpendicular to the conveyance direction.

Also, when liquid droplets will be fired to form an image on a recording medium, according to the apparatus that fires liquid droplets according to the embodiment of the present invention, as a result of the landing position of the fired liquid droplets for each color being controlled with high accuracy, it is possible to reduce a color shift to improve the image quality of the formed image.

<Variants>

Note that, the apparatus that fires liquid droplets according to the embodiment of the present invention may further include other sensors in the configuration illustrated in FIG. 2. For example, the apparatus that fires liquid droplets may further have a sensor on the upstream side of the sensor SENK for black, on the downstream side of the sensor SENY for yellow, or the like. That is, the apparatus that fires liquid droplets may have 5 or more sensors.

The detection apparatus 50 illustrated in FIG. 4 may be implemented by hardware, for example, as illustrated below.

Figure 26:
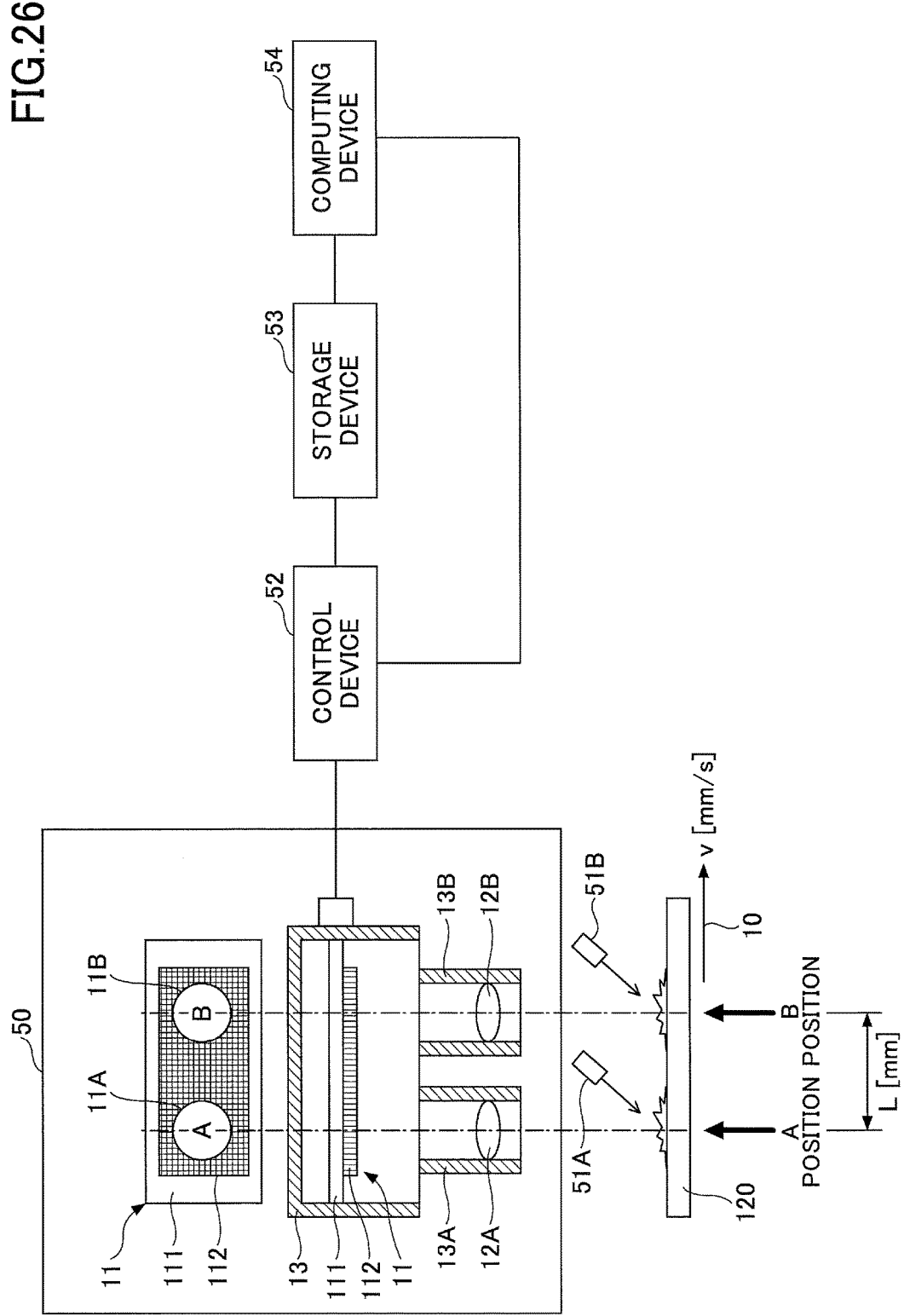
FIG. 26 generally illustrates a first variant of a hardware configuration implementing the detection unit according to the embodiment of the present invention.

FIG. 26 generally illustrates a first variant of a hardware configuration implementing the detection unit according to the embodiment of the present invention. Below, the same reference numerals are given to the same elements as the elements described above, and duplicate description will be omitted.

In comparison to the above-described hardware configuration, for example, the configuration of FIG. 5, the first variant is different in that, in the detection apparatus 50, a plurality of optical systems are included in a single unit. That is, while the above-described hardware configuration is a so-called monocular configuration (see FIG. 5, for example), the hardware configuration of the first variant is a compound-eye configuration.

Also in the first variant, a position at which a first imaging lens 12A on the upstream side will be referred to as the "A position", and a position at which a second imaging lens 12B on the downstream sided of the first imaging lens 12A will be referred to as the "B position", in the compound-eye configuration. Hereinafter, "L" denotes the distance between the first imaging lens 12A and the second imaging lens 12B.

The web 120 to be detected is irradiated with laser light, or the like, from a first light source 51A and a second light source 51B, respectively. A position at which light is irradiated from the first light source is the "A position", and a position at which light is irradiated from the second light source is the "B position".

Each of the first light source 51A and the second light source 51B has a light emittance device that emits laser light and a collimator lens that acquires approximately parallel light from the light emitted by the light emittance device. Also, each of the first light source and the second light source is installed at a position such that the light source will emit laser light toward the surface of the web 120 obliquely.

The detection apparatus 50 includes an area sensor 11, a first imaging lens 12A at a position facing the "A position", and a second imaging lens 12B at a position facing the "B position".

The area sensor 11 is a sensor having a configuration such that, for example, on a silicon substrate 111, an imaging device 112 is formed. Note that, on the imaging device 112, an "A area 11A" and a "B area 11B" are provided to acquire respective two-dimensional images. The area sensor 11 is, for example, a CCD sensor, a CMOS sensor, a photodiode array, or the like. The area sensor 11 is held in a housing 13. The first imaging lens 12A and the second imaging lens 12B are supported by a first lens-barrel 13A and a second lens-barrel 13B, respectively.

In this example, as illustrated, the optical axis of the first imaging lens 12A corresponds to the center of the "A area 11A". In the same way, the optical axis of the second imaging lens 12B corresponds to the center of the "B area 11B". Therefore, the first imaging lens 12A and the second imaging lens 12B form images on the "A area 11A" and the "B area 11B", respectively, to generate respective two-dimensional images.

It is also possible that the detection apparatus 50 has the following configuration, instead.

Figure 27:
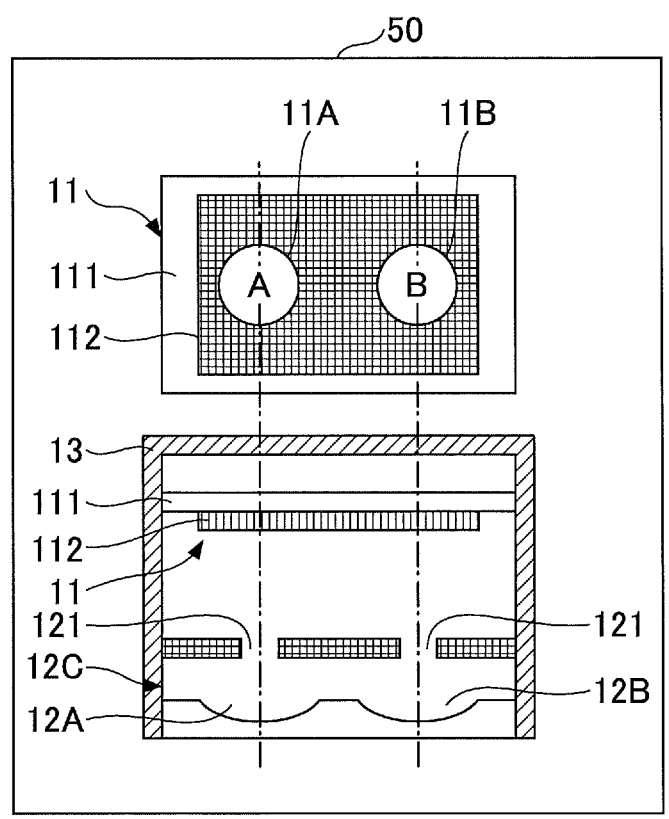
FIG. 27 generally illustrates a second variant of the hardware configuration of the detection unit according to the embodiment of the present invention.

FIG. 27 generally illustrates a second variant of the hardware configuration of the detection unit according to the embodiment of the present invention. Below, the points different from FIG. 26, that is, the hardware configuration of the detection apparatus 50, in particular, will be described. In comparison to the configuration of FIG. 26, the configuration of the detection apparatus 50 is different in that the first imaging lens 12A and the second imaging lens 12B are included into a single lens unit 12C. The area sensor 11, and so forth, for example, have the same configuration as the configuration illustrated in FIG. 26.

Also, in this example, it is desirable that in order to avoid interference between respective images of the first imaging lens 12A and the second imaging lens 12B, apertures 121, or the like, are used. By using the apertures 121, it is possible to restrict respective areas in which the first imaging lens 12A and the second imaging lens 12B form images. Therefore, it is possible to reduce interference between the respective formed images, and the detection apparatus 50 can calculate the moving speed of the web 120 at the upstream sensor position based on the images generated in the "A position" and the "B position". It is also possible to calculate the moving speed of the web 120 in the same way also using the sensor installed at the downstream position. It is also possible that, based on the speed difference between the moving speeds calculated using the upstream-side sensor and the downstream-side sensor, the image forming apparatus controls the timing to fire liquid droplets.

FIGS. 28A and 28B generally illustrate a third variant of the hardware configuration of the detection unit according to the embodiment of the present invention. In comparison to the configuration illustrated in FIG. 27, the configuration of the detection apparatus 50 illustrated in FIG. 28A is different in that the area sensor 11 is a second area sensor 11' different from the area sensor 11 described above. On the other hand, the configuration of the first imaging lens 12A, the second imaging lens 12B, and so forth, for example, is the same as the configuration of FIG. 27.

The second area sensor 11' has a configuration, for example, as illustrated in FIG. 28B, for example. Actually, as illustrated in FIG. 28B, a plurality of imaging devices b are formed on a wafer a. Next, from the wafer a, imaging devices b are cut out, respectively. The first the imaging device 112A and the second the imaging device 112B that are the thus cut out imaging devices are then mounted on the silicon substrate 111. At this time, the positions of the first imaging lens 12A and the second imaging lens 12B are determined according to the space between the first the imaging device 112A and the second the imaging device 112B.

In many cases, imaging devices are manufactured for imaging. Therefore, the ratio between the lengths of the imaging device in the X and Y directions, that is, the aspect ratio, may be, in many cases, determined as a square, "4:3", "16:9", or the like, according to the ratio of an image format. According to the embodiment, images at two or more points spaced at fixed intervals are taken. Actually, images are taken along the X direction from among the two dimensions X and Y, that is, along the conveyance direction 10 (see FIG. 2) at points spaced apart at a fixed interval. In contrast, the above-mentioned imaging devices have aspect ratios according to image formats. Therefore, when imaging is carried out for two points spaced apart at a fixed interval in the X direction as in the embodiment, parts in the imaging device concerning the Y direction may be not used. Also, in order to increase the pixel density, for example, the imaging device having a high pixel density in both the X and Y directions is used, and therefore, the cost may be increased, for example.

By using the illustrated configuration, on the silicon substrate 111, the first the imaging device 112A and the second the imaging device 112B spaced apart at a fixed interval are placed, as illustrated in FIG. 28A. Therefore, the imaging devices concerning the Y direction are not used, and the number of imaging devices can be reduced. Therefore, it is possible to reduce useless imaging devices. Also, because the first imaging device 112A and the second imaging device 112B are produced through a high-preciseness semiconductor process, it is possible to acquire the space between the first imaging device 112A and the second imaging device 112B with high accuracy.

Figure 29:
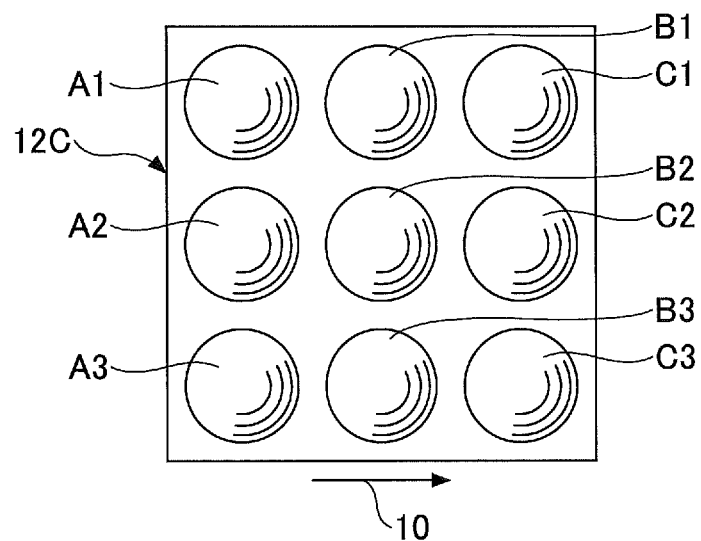
FIG. 29 generally illustrates one example of a plurality of imaging lenses used in the detection unit according to the embodiment of the present invention.

FIG. 29 generally illustrates one example of a plurality of imaging lenses usable in the detection unit according to the embodiment of the present invention. A lens array illustrated in FIG. 29 may be used to implement the detection unit.

The illustrated lens array has such a configuration that two or more lenses are integrated. Actually, the illustrated lens array includes imaging lenses arranged as 3 by 3, i.e., totally, nine imaging lenses A1 through C3, as one example. By using such a lens array, it is possible to take images indicating the corresponding nine points. In this case, an area sensor having nine imaging areas is used.

According to the configuration of FIG. 29, it may be possible that, for example, calculation concerning the two imaging areas can be carried out simultaneously, that is, parallelly, using the lenses included in the lens array. Then, by averaging the respective calculation results or removing errors from the calculation results, the detection apparatus can carry out calculation with high accuracy, improve the calculation stability, and so forth, in comparison to a case of using a single calculation result using a single lens, for example. Also, there is a case where calculation is carried out based on application software where the process speed varies. Also in this case, because the area where the correlation calculation is carried out is increased using the lens array, it is possible to acquire the moving speed calculation with high accuracy.

Note that, a single member may be used as both the first supporting member and second supporting member. For example, the first supporting member and second supporting member may have the following configuration.

Figure 30:
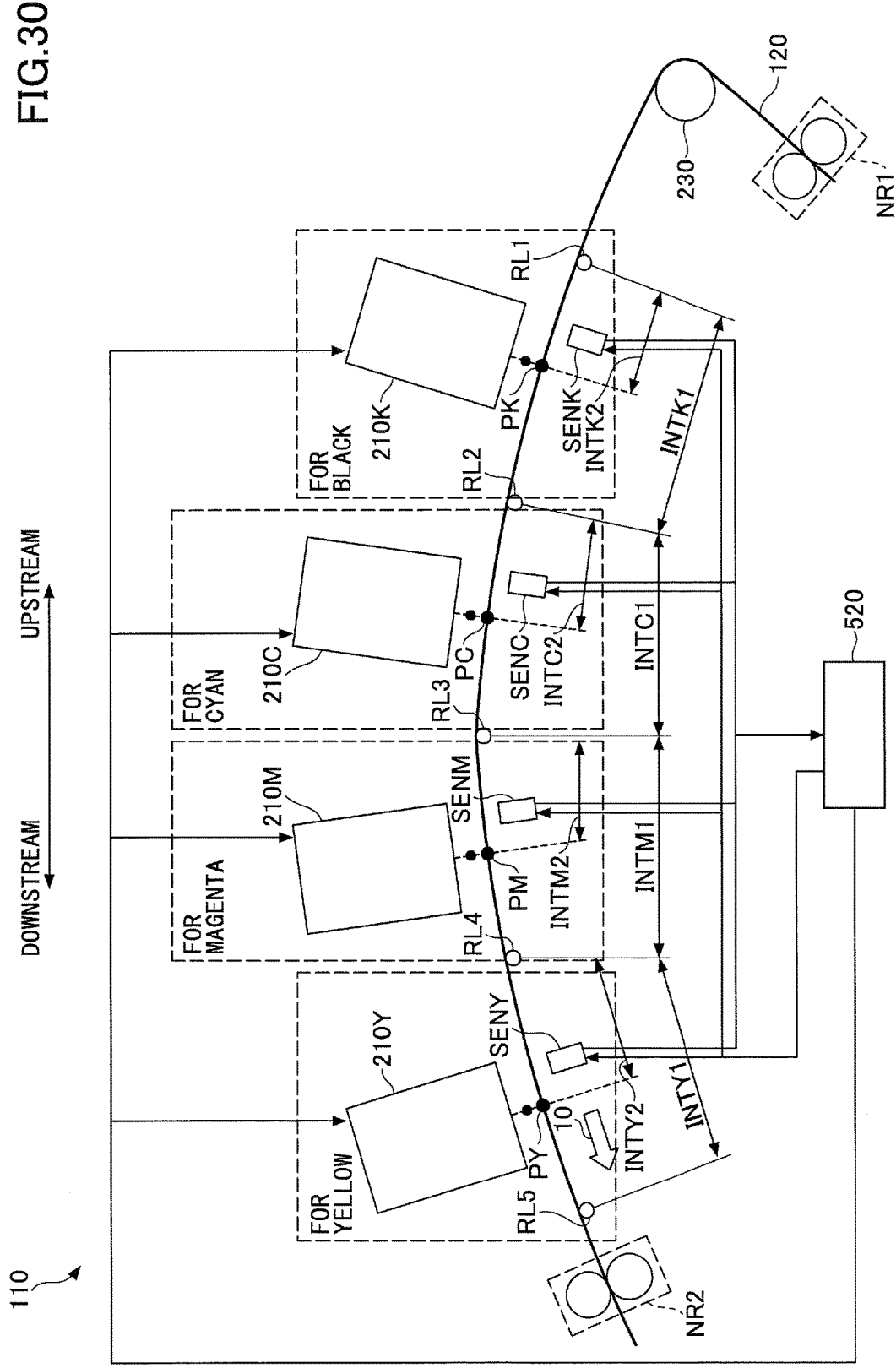
FIG. 30 generally illustrates a variant of the apparatus that fires liquid droplets according to the embodiment of the present invention.

FIG. 30 generally illustrates another variant of the apparatus that fires liquid droplets according to the embodiment of the present invention. In comparison to FIG. 2, the arrangement of the first supporting member and second supporting member is different. As illustrated, the respective first supporting members and respective second supporting members may be implemented by, for example, a first member RL1, a second member RL2, a third member RL3, a fourth member RL4, and a fifth member RL5. That is, a single member may be used as both the second supporting member installed on the downstream side of one liquid firing head unit and the first supporting member installed on the upstream side of a next liquid firing head unit. Note that, a roller may be used as both the second supporting member and first supporting member, or a curved plate may be used as both the second supporting member and first supporting member.

Note that, the apparatus that fires liquid droplets according to the embodiment of the present invention may be implemented by a system having one or more apparatus that fires liquid droplets. For example, the apparatus that fires liquid droplets may be implemented by a system including a housing in which the black liquid firing head unit 210K and the cyan liquid firing head unit 210C are included and another housing in which the magenta liquid firing head unit 210M and the yellow liquid firing head unit 210Y are included.

Also, in the apparatus that fires liquid droplets and the system that fires liquid droplets according to the embodiments of the present invention, the liquid is not limited to ink, and may be another recording liquid, a fixing processing liquid, or the like. That is, the apparatus that fires liquid droplets and the system that fires liquid droplets according to the embodiments of the present invention may be applied to apparatuses and systems that fire liquid droplets other than ink droplets.

Therefore, the apparatuses that fire liquid droplets and the systems that fire liquid droplets according to the embodiments of the present invention are not limited to apparatuses and systems that form images. For example, the apparatuses that fire liquid droplets and the systems that fire liquid droplets according to the embodiments of the present invention may be applied to apparatus and systems forming three-dimensional objects, or the like.

Also, the conveyed object is not limited to a recording medium such as a paper. The conveyed object may be any material to which liquid can adhere. For example, the materials to which liquid can adhere include paper, string/thread, fiber, fabric/cloth, leather, metal, plastic, glass, wood, ceramics, any combinations thereof, and so forth, to which liquid can adhere even temporarily.

Also, the embodiments of the present invention can also be applied to apparatuses which carry out some processing on to a conveyed object using line-shaped head units each of which extends in a direction perpendicular to a conveyance direction, the line-shaped head units being arranged in the conveyance direction.

For example, any of the embodiments of the present invention may be applied to a conveyance apparatus in which a head unit emits laser light to carry out patterning processing on a substrate that is a conveyed object using the laser light, or the like. Actually, the conveyance apparatus has laser heads each extending in a direction perpendicular to a conveyance direction, the laser heads being arranged in the conveyance direction in which the substrate is conveyed. Then, the conveyance apparatus detects the position of the substrate, for example, and moves the head units according to the detection results. Also, in this example, the processing position is the position at which the substrate is irradiated with the laser light.

Also, the number of head units that the conveyance apparatus has is not limited to two or more. That is, the embodiments of the present invention may be applied to cases where processing is carried out continuously on a conveyed object at a reference position, for example.

Also, according to the embodiments of the present invention, it is also possible to implement, by a program, some or all of the steps of the method for firing liquid droplets using the conveyance apparatus, the system including one or more information processing apparatuses, or any combination thereof.

According to the embodiments of the present invention, it is possible to detect a position of a conveyed object, or the like, with high accuracy.

The conveyed object detection apparatuses, the conveyance apparatuses, and the conveyed object detection methods have been described in the embodiments. However, embodiments are not limited to the above-described embodiments, and various modifications and replacements may be made.

What is claimed is:

1. A conveyed object detection apparatus comprising:
   an optical sensor configured to receive light reflected by a conveyed object;
   a detection unit configured to use the optical sensor to acquire a detection result indicating a position, a moving speed, or a moved amount of the conveyed object in at least one of a conveyance direction in which the conveyed object is conveyed and a direction perpendicular to the conveyance direction, or a combination of the position, the moving speed, and the moved amount; and
   a setting unit configured to set an aperture value and an exposure time concerning the optical sensor based on the detection result.

2. The conveyed object detection apparatus according to claim 1, wherein
   the setting unit is further configured to receive, from outside, a speed at which conveyed object is conveyed.

3. The conveyed object detection apparatus according to claim 1, wherein
   the setting unit is further configured to set the aperture value and the exposure time based on the moving speed of the conveyed object.

4. The conveyed object detection apparatus according to claim 1, wherein
   the detection unit is further configured to acquire the detection result based on a pattern that the conveyed object has.

5. The conveyed object detection apparatus according to claim 4, wherein
   the pattern is generated from interference occurring as a result of unevenness that the conveyed object has being irradiated with light, and
   the detection unit is further configured to acquire the detection result based on an image acquired from taking the image of the pattern.

6. The conveyed object detection apparatus according to claim 4, wherein
   the detection unit is further configured to acquire the detection result based a result of detecting the pattern at two or more different timings.

7. A conveyance apparatus comprising:
   the conveyed object detection apparatus according to claim 1;
   a head unit configured to carry out a process on the conveyed object; and
   a control unit configured to control operation of the head unit to carry out the process based on the detection result of the conveyed object detection apparatus.

8. The conveyance apparatus according to claim 7, wherein
   a plurality of the detection units are provided for a plurality of the head units, respectively,
   the detection units are provided between first supporting members and second supporting members, respectively,
   the first supporting members are provided on upstream sides of positions where the head units carry out the processes, respectively, and are configured to convey the conveyed object, and
   the second supporting members are provided on downstream sides of the positions where the head units carry out the processes, respectively, and are configured to convey the conveyed object.

9. The conveyance apparatus according to claim 8, wherein
the detection units are further configured to be provided between the positions where the head units carry out the processes and the first supporting members, respectively.

10. The conveyance apparatus according to claim 8, further comprising:
moving units each configured to move a corresponding one of the head units, respectively, in the direction perpendicular to the conveyance direction.

11. The conveyance apparatus according to claim 8, wherein
each of the head units is further configured to be controlled, based on a corresponding one of the detection results in the conveyance direction, to carry out a corresponding one of the processes on the conveyed object.

12. The conveyance apparatus according to claim 7, further comprising:
a moving unit configured to move the head unit in the direction perpendicular to the conveyance direction.

13. The conveyance apparatus according to claim 7, wherein
the head unit is further configured to be controlled, based on the detection result in the conveyance direction, to carry out the process on the conveyed object.

14. The conveyance apparatus according to claim 7, wherein
the conveyed object is a continuous sheet extending along the conveyance direction.

15. The conveyance apparatus according to claim 7, wherein
as a result of the process being carried out, an image is formed on the conveyed object.

16. The conveyed object detection apparatus according to claim 1, further comprising a diaphragm control unit configured to control an actuator to change a diaphragm to change the aperture value and the exposure time.

17. A conveyed object detection method comprising:
receiving, by an optical sensor, light reflected by a conveyed object;
using the optical sensor to acquire a detection result indicating a position, a moving speed, or a moved amount of the conveyed object in at least one of a conveyance direction where the conveyed object is conveyed and a direction perpendicular to the conveyance direction, or a combination of the position, the moving speed, and the moved amount; and
setting an aperture value and an exposure time concerning the optical sensor based on the detection result.

\* \* \* \* \*